US008216825B2

(12) United States Patent
Yuan

(10) Patent No.: US 8,216,825 B2
(45) Date of Patent: Jul. 10, 2012

(54) AQUACULTURE BIOCIDE METHODS AND COMPOSITIONS

(76) Inventor: Alex Yuan, Portland, OR (US)

( * ) Notice: Subject to any disclaimer, the term of this patent is extended or adjusted under 35 U.S.C. 154(b) by 12 days.

(21) Appl. No.: 12/932,874

(22) Filed: Mar. 7, 2011

(65) Prior Publication Data

US 2012/0073021 A1 Mar. 22, 2012

Related U.S. Application Data

(60) Provisional application No. 61/384,292, filed on Sep. 19, 2010.

(51) Int. Cl.
*C12N 1/12* (2006.01)
*A01H 13/00* (2006.01)
(52) U.S. Cl. ............... 435/257.1; 435/257.3; 435/257.5; 435/261; 800/296
(58) Field of Classification Search .................. 800/296; 435/257.1, 257.3, 257.5, 261
See application file for complete search history.

(56) References Cited

U.S. PATENT DOCUMENTS

| | | | |
|---|---|---|---|
| 5,194,264 | A | 3/1993 | Van Tonder et al. |
| 5,792,750 | A | 8/1998 | Borovsky et al. |
| 2009/0126260 | A1 | 5/2009 | Aravanis et al. |
| 2009/0280545 | A1* | 11/2009 | Mendez et al. ............... 435/157 |
| 2010/0196995 | A1 | 8/2010 | Weissman et al. |

OTHER PUBLICATIONS

Moreno-Garrido, J. et al. Aquacultural Engineering (2001) vol. 24; pp. 107-114.*
Euractiv: Letters to the Editor. Klock, G. It's the process, stupid. Biofuels from microalgae are not yet sustainable. Published online: Jan. 6, 2010, pp. 1-4.*
Canadian Council of Ministers of the Environment (2007) Canadian Water Quality Guidelines for the Protection of Aquatic Life; Methoprene, pp. 1-11.*
Bayer Garden. Safety data sheet: green cleaner. 2009; 1-7. www.capitalgardens.co.uk/images/bayergarden/79475756.pdf.
Bayer Material Science. Material safety data sheet: SFCIII 2.7 pour taxidermy. 2009; 1-11. www.baycareonline.com/nafta/MSDS/80757361.pdf.
Filipsson, et al. Concise international chemical assessment Document 5: Limonene. World Health Organization. 1998; 1-36. www.whqlibdoc.who/int/publications/1998/9241530057.pdf.
International search report and written opinion dated Jun. 15, 2011 for PCT/US2011/027447.
Liwarska-Bizukojc, et al. Acute toxicity and genotoxicity of five selected anionic and nonionic surfactants. Chemosphere. 2005; 58(9):1249-1253.
Stewart. Toxicological results of NeemAzal technical and NeemAzal formulations. Practice oriented results on use and production of Neem-ingredients and pheromones. Proceedings of the 7th workshop. Kleeberg. 1997; 21-26.
Agh, et al. Handbook of protocols and guidelines for culture and enrichment of live food for use in larviculture. Artemia and Aquatic animals research center. Mar. 2005.
Ajah. Mass culture Rotifera (*Brachionus quadridentatus* [Hermann, 1783]) using three different algae species. African J of Food Science. 2010; 4(3):80-85.
Altocid Pro-G 2.5#. (2010). Retrieved Aug. 28, 2010 from Pest Control Supplies website: www.pcspeststore.com/ProductDetails.asp?ProductCode=ALTOG.
Alvarado-Flores, et al. Immunodetection of Luteinizing Hormone (LH), Follicle-Stimulating Hormone (FSH), Thyroid Stimulating Hormone (TSH) and Prolactin (PRL) in *Brachionus calyciflorus* (Rotifera: Monogononta). Rev Biol Trop. 2009; 57(4):1049-1058.
Antunes-Kenyon, et al. Methoprene: A review of the impacts of the insect growth regulator methoprene on non-target aquatic organisms in fish bearing waters. Massachusetts Pesticide Bureau, DFA. Aug. 2001.
Arbuckle, et al. (2001). An exploratory analysis of the effect of pesticide exposure on the risk of spontaneous abortion in an Ontario farm population. Environmental Health Perspectives, 109(8), 851-7.
Becker, E. W. (1994). Microalgae: biotechnology and microbiology. Melbourne: Cambridge University Press. ISBN: 0-521-35020-4.
Ben-Amotz, A. (2008). Production of Microalgae in Open Ponds. [Presentation], Retrieved from NREL website: www.nrel.gov/biomass/pdfs/abstracts.pdf.
Benemann, et al. Systems and economic analysis of microalgae ponds for conversion of Co2 to biomass. UC Berkeley. Jan. 15, 1994.
Benemann. Overview: Algae oil to biofuels. Benemann associates. Annotated presentation. NREL-AFOSR Workshop, Algal Oil for Jet Fuel Production, Arlington, VA. Feb. 19, 2008. Available at http://www.nrel.gov/biomass/pdfs/benemann.pdf.
Bennett, et al. A demographic profile of the fastest growing metazoan: a strain of*Brachionus calycifcrus* (Rotifera). Oikos. 1989; 55: 365-369.
Bhunia, et al. Growth, chlorophyll a content, nitrogen-fixing ability, and certain metabolic activities of *Nostoc muscorum*: effect of methylparathion and benthiocarb. Bull Environ Contam Toxicol. Jul. 1991;47(1):43-50.
Borovsky, et al. Characterization and localization of mosquito-gut receptors for trypsin modulating oostatic factor using a complementary peptide and immunocytochemistry. FASEB J. Mar. 1, 1994;8(3):350-5.
Burlew, et al. Algal culture from laboratory to pilot plant. Carnegie institution of Washington publication, May 1976.
Calleja, et al. Comparative Acute Toxicity of the First 50 Multicentre Evaluation of In Vitro Cytotoxicity Chemicals to Aquatic Non-Vertebrates. Arch. Environ. Contam. Toxicol. 1994; 26:69-78.
Campiche. Endocrine Disruption in Soil Invertebrates: Assessing Multigeneration Effects of Insect Growth Regulators on *Folsomia candida* Developing a Toxicoproteomic Approach. Ecole Polytechnique Federale de Lausanne. 2006.
Canadian Council of Ministers of the Environment. 2007. Canadian Water Quality Guidelines for the Protection of Aquatic Life: Methoprene. In Canadian environmental quality guidelines, 1999, Canadian Council of Ministers of the Environment, Winnipeg.
Carbaryl; Updated Toxicology Disciplinary Chapter for the Reregistration Eligibility Decision Document. Docket ID# OPP-2002-0138-0008 U.S. Environmental Protection Agency, Office of Pesticide Programs, Health Effects Division. (n.d.). Available at cascade.epa.gov/RightSite/dk_public_collection_item_detail.htm?ObjectType=dk_docket_item&cid=OPP-2002-0138-0008&ShowList=xreferences&Action=view., in National Pesticide Information Center. (n.d.). Carbaryl general fact sheet. Retrieved from NPIC website: npic.orst.edu/factsheets/carbgen.pdf. Accessed Apr. 6, 2011.

(Continued)

*Primary Examiner* — Russell Kallis
(74) *Attorney, Agent, or Firm* — Wilson Sonsini Goodrich & Rosati

(57) ABSTRACT

Methods and compositions for increasing the productivity of algae cultures by controlling grazers are described herein.

11 Claims, 5 Drawing Sheets

OTHER PUBLICATIONS

Chang, et al. Impact of pesticide application on zooplankton communities with different densities of invertebrate predators: an experimental analysis using small-scale mesocosms. Aquat Toxicol. May 15, 2005;72(4):373-82.

Chisti. Biodiesel from microalgae. Biotechnol Adv. May-Jun. 2007;25(3):294-306.

Clark, R. (2009). Can we make biofuels work? National Geographic, "Energy for Tomorrow: Repowering the Planet," 72-73.

Clegg, et al. The effect of Four Chlorinated Hydrocarbon Pesticides and One Organophosphate Pesticide on ATP Levels in Three Species of Photosynthesizing Freshwater Algae. Bot. Gaz. 1974; 135(4):368-372.

Correa-Reyes, et al. Nonylphenol algal bioaccumulation and its effect through the trophic chain. Chemosphere. Jun. 2007;68(4):662-70.

Cox. Nonyl Phenol and Related Chemicals. J Pest Reform. 1996; 16(1):15-20.

Csondes, A. Environmental Fate of Methoprene. Environmental Monitoring Branch Department of Pesticide Regulations. Nov. 11, 2004.

De-Bashan, et al. Increased pigment and lipid content, lipid variety and cell and population size of the microalgae *Chlorella* spp when co-immobilized in alginate beads with the microalgae-growth-promoting bacterium *Azospirillum brasilense*. Can. J. Micro. 2002; 48:514-521.

DeLorenzo, et al. Toxicity of pesticides to aquatic microorganisms: a review. Environ Toxicol Chem. Jan. 2001;20(1):84-98.

Edmondson, W. Reproductive rate of planktonic rotifers as related to food and temperature in nature . Ecol. Mo- nogr. 35: 61-111, (1965).

Ehrenberg, R. (Aug. 2009). The biofuel future. Science News, 176, 24-29.

EPA. Aquatic Life Ambient Water Quality Criteria-Nonylphenol Final. US EPA. Dec. 2005.

Ephemeronium, et al. (Jul. 9, 2010). Ball-and-stick model of the methoprene molecule. [image]. Retrieved Aug. 28, 2010 from Wikipedia website: en.wikipedia.org/wiki/File:Methoprene-3D-balls.png.

Epp, et al. Osmotic regulation of the Brackish-water Rotifer *Brachionus plicatilis* (Muller). J Exp Biol. 1977; 68:151-156.

Fang, et al. A suppressor screen in chlamydomonas identifies novel components of the retinoblastoma tumor suppressor pathway. Genetics. Mar. 2008;178(3):1295-310.

Fernández-Casalderry, et al. Acute toxicity of several pesticides to rotifer (*Brachionus calyciflorus*). Bull Environ Contam Toxicol. Jan. 1992;48(1):14-7.

Fink. Pyrethroids. Biol 564 presentation. Apr. 29, 2008.

Gallardo, et al. Effect of juvenile hormone and serotonin (5-HT) on mixis induction of the rotifer *Brachionus plicatilis* Muller. J Exp Mar Bio Ecol. Sep. 5, 2000;252(1):97-107.

Gallardo, et al. Effect of some vertebrate and invertebrate hormones on the population growth, mictic female production, and body size of the marine rotifer *Brachionus plicatilis* Müller. Hydrobiologia. Dec. 1997; vol. 358, Nos. 1-3, 113-120.

Gardes, et al. Diatom-associated bacteria are required for aggregation of *Thalassiosira weissflogii*. The ISME Journal. 2010; 1-10.

Gates, P. (May 7, 2009). Klingon Warship. [Web log message]. Retrieved from http://beyondthehumaneye.blogspot.com/2009/05/klingon-warship.html.

Gates, P. (Photographer). (2009). Keratella. [Web image]. Retrieved from http://beyondthehumaneye.blogspot.com/search?updated-max=2009-05-09T21%3A34%3A00%2B01%3A00&max-results=10.

Gershenzon, et al. The function of terpene natural products in the natural world Nature Chemical Biology. 2007; 3(7):408-414.

Gilbert. Female polymorphism and sexual reproduction in the rotifer asplanchna: evolution of the relationship and control by dietary tocopherol. American Naturalist. 1980; 116(3):409-431.

Glare, et al. Environmental and health impacts of the insect juvenile hormone analogue, S-methoprene. Biocontrol and Biodiversity. Mar. 1999.

Grobbelaar, J.U. (1981). Infections: Experiences in miniponds. In: Grobbelaar J.U., Soeder C.J. and Toerien D.F. (eds), Wastewater for Aquaculture. Series C, No. 3. University of the OFS Publ., Bloemfontein, South Africa, 116-123.

Gupta, et al. Biopesticides: An ecofriendly approach for pest control. J Biopesticides. 2010; 3(1):186-188.

Haberman, et al. On characteristics reflecting the trophic state of large and shallow Estonian lakes (L. Peipsi, L. Vortsjarv). Hydrobiologica. 2003; 506-509:737-744.

Hagiwara, et al. Feeding History and Hatching of Resting Eggs in the Marine Rotifer *Brachionus plicatilis*. 1990; 56(12):1965-1971.

Hansson, et al. Size structure and succession in phytoplankton communities: the impact of interactions between herbivory and predation. OIKOS. 1998; 81:337-345.

Harris, et al. Insect Growth Regulators (IGRs). Chase Research Gardens Inc., (2010).

Hasler, et al. Demonstration of the Antagonistic Action of Large Aquatic Plants on Algae and Rotifers. Ecology. 1949; 30(3):359-364.

Helling, et al. Algae Bioassay Detection of Pesticide Mobility in Soils. Weed Science. 1971; 19(6):685-690.

Hirayama, et al. Fundamental Studies on Physiology of Rotifer for its Mass Culture—I Filter Feeding of Rotifer. 1972; 38(11):1207-1214.

Ho. Improvement of Algae Settleability in High Rate Ponds Using Rotifers. Richmond Field Station, UC Berkeley, (May 2001).

Hosfelt. Azadirachtin. Chemistry 150. 2008.

Illinois Department of Public Health. (2007). Pyrethroid Insecticides. Environmental Health Fact Sheet. Accessed Aug. 4, 2010, at http://www.idph.state.il.us/envhealth/factsheets/pyrethroid.htm.

Jackson, G. Coagulation of marine algae. Journal Title Advances in chemistry series. 1995; 244:203-217.

James, et al. Intensive rotifer cultures using chemostats. Hydrobiologia. 1989; 186-187(1): 423-430.

Kaiser, et al. Correlations of *Vibrio fischeri* bacteria test data with bioassay data for other organisms. Environ Health Perspect. Apr. 1998;106 Suppl 2:583-91.

Kamei, et al. Concentration and residual efficacy of methoprene in a running ditch. Journal of Pesticide Science. 1992; vol. No. v. 17(3) p. 155-159.

Kamiyama, et al. Lethal effect of the dinoflagellete *Heterocapsa circularisquama* upon the tintinnid ciliate *Favella taraikaensis*. Mae Ecol Prog Ser. 1997; 160:27-33.

Kim, et al. Cytotoxic action mode of a novel porphyrin derivative isolated from harmful red tide dinoflagellate *Heterocapsa circularisquama*. J Biochem Mol Toxicol. May-Jun. 2008;22(3):158-65.

Kim, et al. Specific Toxic Effect of Dinoflagellete *Heterocapsa circularisquama* on the rotifer *Brachionus plicatilis*. Biosci Biotechno Biochem. 2000; 64(12):2719-2722.

Kleeberg. Practice Oriented Results on Use and Production of Neem-Ingredients and Phermones. 7th Workshop Wetzler, Germany. 1997.

Larsdotter. (2006). Wastewater treatment with microalgae—a literature review. Vatten, 62, 31-38.

Lee, et al. (1998). Rapid method for the determination of lipid from the green alga *Botryococcus braunii*. Biotechnology Techniques,12(7), 553-556.

Ley, S. Synthesis and chemistry of the insect antifeedant azadirachtin. Pure and Applied Chemistry. 1994; 66(10/11):2099-2102.

Li, et al. Comparison of growth and lipid content in thre *Botryococcus braunii* strains. J. App. Phyc. 2005; 17:551-556.

Liang, et al. Biomass and lipid productivities of *Chlorella vulgaris* under autotrophic, heterotrophic and mixotrophic growth conditions. Biotechnol Lett. Jul. 2009;31(7): 1043-9.

Lindemann, et al. A study of rotifer feeding and digestive processes using erythrocytes as microparticulate markers. Hydrobiologia. 2000; 435(1-3):27-41.

Lopez, et al. New trends in pest control: the search of greener insecticides. Green Chem: 2005; 7:431-442.

Lowe, et al. Evidence that the rotifer *Brachionus plicatilis* is not an osmoconformer. Mar Bio. 2005; 146:923-929.

Lurling, M. Investigation of a rotifer (*Brachionus calyciflorus*)—green alga (*Scenedesmus pectinatus*) interaction under non- and nutrient-limited conditions. Ann. Limnol.—Int. J. Lim. 2006; 42(1):9-17.

Malathion: Revised human health risk assessment for the reregistration eligibility decision document (RED); EPA-HQ-OPP-2004-0348-0057; U.S. Environmental Protection Agency, Office of Prevention, Pesticides and Toxic Substances, Office of Pesticide Programs, U.S. Government Printing Office: Washington, DC, 2006., in National Pesticide Information Center. (n.d.). Malathion technical fact sheet. Retrieved from NPIC website: npic.orst.edu/factsheets/malatech.pdf.

Manaffar, et al. Effect of *Azadirachta indica* seed extract upon predator ciliates on intensive culture of unicellular algae *Dunaliella tertiolecta*. Pajouhesh-VA-Sazandegi Summer 2006; 18(2 (71 in Animal and Fisheries Sciences)):82-88.

Maniago. (Nov. 21, 2007). A window with a insect screen. [image]. Retrieved Sep. 9, 2010 from Wikipedia website: en.wikipedia.org/wiki/File:Window_with_insect_screen.JPG.

Marcial, et al. Effect of some pesticides on reproduction on rotifer *Brachionus plicatilis* Muller. Hydrobiologica. 2005; 546:569-575.

Mark-Welch, et al. Cytogenetic evidence for asexual evolution of bdelloid rotifers. PNAS. 2004; 101(6):1618-1621.

Matsuyama. Harmful Effect Dinoflagellete *Heterocapsa circularisquama* on Shellfish Squaculture in Japan. JARQ. 1999; 33:283-293.

Mitchell. The effect of pH on *Brachionus calyciflorus* Pallus (rotifera). Hydrobiologia. 1992; 245:87-93.

Mordue, et al. Azadirachtin from Neem Tree *Azadirachta indica*: its action against insects. An. Soc. Entomol. Brasil. 2000: 29(4);615-632.

Moreno-Garrido, et al. (2001). Assessing chemical compounds for controlling predator ciliates in outdoor mass cultures of the green algae *Dunaliella salina*. Aquacultural Engineering, 24(2), 107-114.

Muralikrishna, et al. Effect of Insecticides on Soil Algae Population. Bull. Environ. Contam. Toxicol. 1984; 33:241-245.

Mykles, et al. Neuropeptide Action in Insects and Crustaceans. Arthropod Neuropeptide Action. 2010; 836-846.

National Pesticide Information Center (n.d.). Glyphosate Technical Fact Sheet. Retrieved Oct. 30, 2010 from NPIC website: http://npic.orst.edu/factsheets/glyphotech.pdf.

Toynton, K. et al. (2009) National Pesticide Information Center. (n.d.). Permethrin technical fact sheet. Retrieved from NPIC website: http://npic.orst.edu/factsheets/Permtech.pdf.

Nico, et al. (May 5, 2010). Gambusia affinis. [image]. Retrieved Sep. 9, 2010 from U.S. Geographical Survey website: http://nas.er.usgs.gov/queries/factsheet.aspx?SpeciesID=846.

Oros, et al. Pyrethroid insecticides: An analysis of use patterns, distributions, potential toxicity and fate in the Sacramento-San Joaquin Delta and Central Valley. White paper for the Interagency Ecological Program. SFEI Contribution 415. San Francisco Estuary Institute, Oakland, CA. 2005.

Pagano, M. Feeding of tropical cladocerans (*Moina micrura*, *Diaphanosoma excisum*) and rotifer (*Brachionus calyciflorus*) on natural phytoplankton: effect of phytoplankton size—structure. J. Plankton Res. 2008;30(4): 401-414.

Passow. Transparent exopolymer particles (TEP) in aquatic environments. Progress in Oceanography. 2002; 55:287-333.

Pest Management Regulatory Agency (Canada). Proposed acceptability for continuing registration—Re-evaluation of S-methoprene. PACR2007-01. Jan. 3, 2007.

Pimentel, D. Ecological effects of pesticides on non-target species. Executive Office of the President Office of Science and Technology (Washington). Jun. 1971.

Pozuelo, et al. Asexual and sexual reproduction in the rotifer *Brachionus plicatilis* cultured at different salinities. Hydrobiologia. 1993; 255-256(1):139-143.

Preston, et al. Use of Freshwater Rotifer *Brachionus calyciflorus* in Screening Assay for Potential Endocrine Disruptors. Environ Toxicol Chem. 2000; 19(12):2923-2928.

Quistad, et al. Environmental degradation of the insect growth regulator (Isopropyl (2E,4E)-11-methoxy-3,7,11-trimethyl-2,4-dodecadienoate). III. Photodecomposition. J Agric Food Chem. 1975; 23(3):299-303.

Quistad, et al. Environmental degradation of the insect growth regulator methoprene (isopropyl (2E,4E)-11-Methoxy-3,7,11-trimethyl-2,4-dodecadienoate). I. Metabolism by alfalfa and rice. J Agric Food Chem. Jul.-Aug. 1974;22(4):582-9.

Quistad, et al. Environmental degradation of the insect growth regulator methoprene. VIII. Boving metabolism to natural products in mild and blood. J Agric Food Chem. Jul.-Aug. 1975;23(4):750-3.

Radix, et al. Reproduction disturbances *Brachionus calyciflorus* (rotifer) for the screening of environmental endocrine disrupters. Chemosphere. 2002; 47:1097-1101.

Resmethrin. Toxnet—Toxicology Data Network. Available at http://toxnet.nlm.nih.gov/cgi-bin/sis/search/f?./temp/~89vjmG:1. Accessed Apr. 30, 2010.

Robertson, et al. (2008). Sustainable biofuels redux. Science, 322, 49-50.

Roe, et al. Invisible Proteins: Novel Delivery System for the Stabilization and Enhanced Activity of Protein Insecticides. 2009 Beltwide Cotton Conferences, San Antonio, Texas, Jan. 5-8, 2009, pp. 834-843.

Roex, et al. Ratios between acute aquatic toxicity and effects on population growth rates in relation to toxicant mode of action. Environmental toxicology and chemistry. 2000; 19(3,): 685-693.

Salomon, et al. Sensitivity of *Chlorella vulgaris* and *Scenedesmus quadricauda* to cypermetrin. Preliminary phase. Sertox. 2003. (in Spanish with English abstract).

Sanchez-Fortun, et al. Comparative study on the environmental risk induced by several pyrethroids in estuarine and freshwater invertebrate organisms. Chemosphere. Apr. 2005;59(4):553-9.

Sato, et al. Photosensitizing hemolytic toxin in *Heterocapsa circularisquama*, a newly identified harmful red tide dinoflagellate. Aquat Toxicol. Feb. 2002;56(3):191.-6.

Schooley, et al. Enviromental degradation of the insect growth regulator methoprene (isopropyl (2E, 4E)-11-methoxy-3,7,11-trimethyl-2,4-dodecadienoate). II. Metabolism by aquatic microorganisms. J Agric Food Chem. Mar.-Apr. 1975;23(2):293-8.

Schooley, et al. Metabolism of Insect Growth Regulators in Aquatic Organisms. ACS Symposium Series. 1979; 99:161-176.

Snell, et al. Effect of progesterone on sexual reproduction of *Brachionus manjavacus* (Rotifera). J Exp Mar Bio Eco. 2008; 363:104-109.

Snell, et al. Genetic determinants of mate recognition *Brachionus manjavacus* (Rotifera). BMC Biology. 2009; 7(60):1-12.

Snell. A review of molecular mechanisms of monogonont rotifer reproduction. Hydrobiologia. 2011; 662: 89-97.

Snell. Chemical ecology of rotifers. Hydrobiologia. 1998; 387/388:267-276.

Stubbins. Virginia Coastal Energy Rearch Consortium Final Report: Algal Biodiesel Studies. Final Version. Dec. 3, 2009.

Sugumar, et al. Induction of population growth, mictic female production and body size by treatment of a synthetic GnRH analogue in the freshwater rotifer, *Brachionus calyciflorus* Pallas. Aquaculture. 2006; 258, Issues 1-4:529-534.

Tanaka, et al. Effect of Alkylphenols on Motility of Unicellular Green Algae *Chlamydomonas reinhardtii* and Crustacea *Daphnia magna*. Journal of Japan Society on Water Environment. 2005; 28(5):333-338. (in Japanese with English abstract).

Tanaka, et al. Toxicity of Alkylphenols to Unicellular Green Algae *Chlamydomonas reinhardtii*. Journal of Japan Society on Water Environment. 2002; 25(1):39-45. (in Japanese with English abstract).

Tessier, A. Comparative population regulation of two planktonic Cladocera (*Holopedium gibberum* and *Daphnia catawba* ). Ecology. vol. 67, No. 2, pp. 285-302. 1986.

Tillmann. Interactions between planktonic microalgae and protozoan grazers. J Eukaryot Microbiol. 2004; 51(2):156-68.

U. S. Environmental Protection Agency. (2006). Registration eligibility decision for propylene glycol. Washington, DC: Office of Prevention, Pesticides, and Toxic Substances. Retrieved Aug. 28, 2010 from USEPA website: http://www.epa.gov/oppsrrd1/REDs/propylene_glycol_red.pdf.

U. S. Environmental Protection Agency. 2006. Reregistration Eligibility Decision (RED): Resmethrin; EPA 738-R-06-003; Office of Prevention, Pesticides and Toxic Substances, Office of Pesticide Programs, U.S. Government Printing Office: Washington, DC. Retrieved Feb. 23, 2011 from USEPA website: http://www.epa.gov/oppsrrd1/REDs/resmethrin_red.pdf.

U.S. Environmental Protection Agency. 2001. Jun. 2001 update of the Mar. 1991 Methoprene R.E.D. Factsheet. Retrieved Aug. 26, 2010 from USEPA website: http://www.epa.gov/oppbppd1/biopesticides/ingredients/factsheets/factsheet_105401.pdf.

Wheeler, et al. A perspective for understanding the modes of juvenile hormone action as a lipid signaling system. Bioessays. Oct. 2003;25(10):994-1001.

Wijffels. Potential of sponges and microalgae for marine biotechnology. Trends in Biotechnology. 2007; 26(1):26-31.

Wolterink, et al. Toxicology evaluations: Methoprine and S-Methoprine. 2001. www.inchem.org/documents/jmpr/jmpmono/2001pr09.htm#2.1.

Yasuno, et al. Effects of permethrin on phytoplankton and zooplankton in an enclosure ecosystem in a pond. Hydrobiologica. 1988; 159:247-258.

Yoshimura, et al. A novel culture system for the ultra-high-density production of the rotifer, *Brachionus rotundiformus*—a preliminary report. Aquaculture. 2003; 227:165-172.

Zou, E. Current status of environmental endocrine disruption in selected aquatic invertebrates. Current Zoology(formerly Acta Zoologica Sinica). Oct. 2003, 49(5): 551-565.

Zwengar, et al. Plant terpenoids: applications and future potentials Biotechnology and Molecular Biology Reviews vol. 3 (1), pp. 001-007, Feb. 2008.

* cited by examiner

Specific Growth Rate Between Days 5 and 12

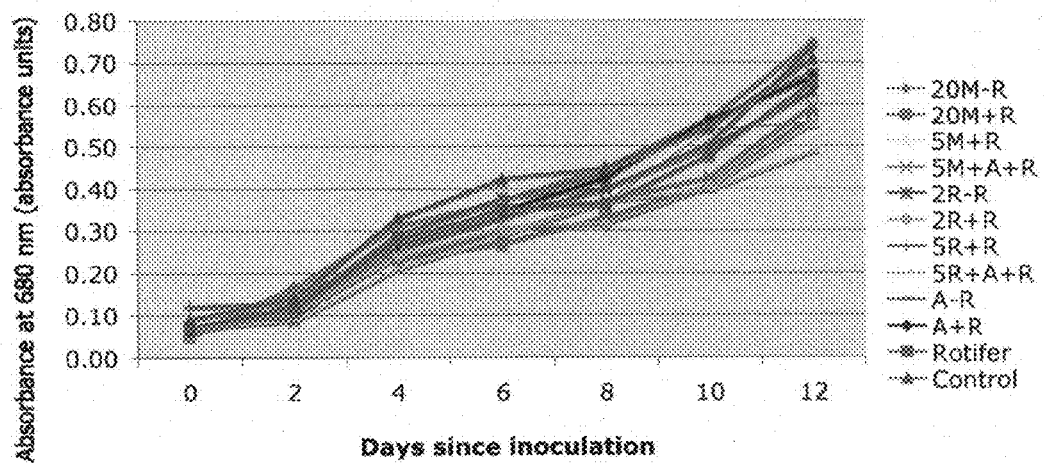
Figure 3. Algal optical density in all groups during the test period.
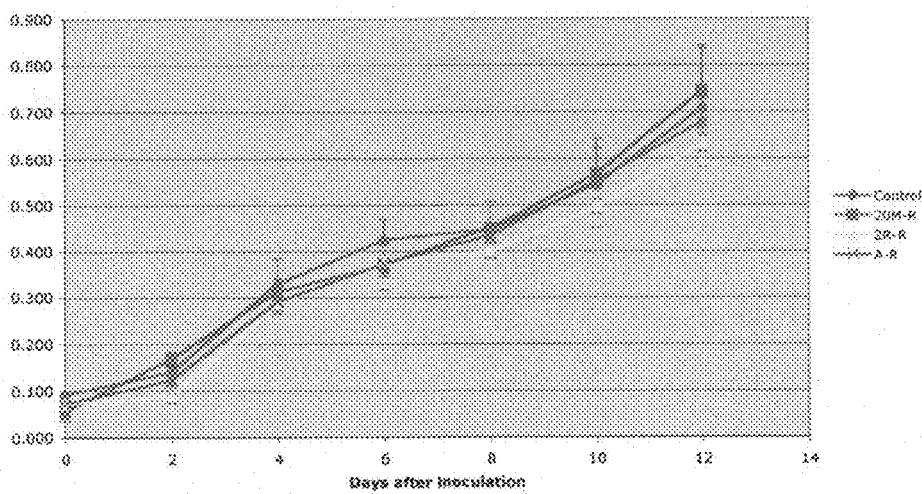
Figure 4. Algal optical density in groups without rotifers.
Y-axis error bars represent one standard deviation.

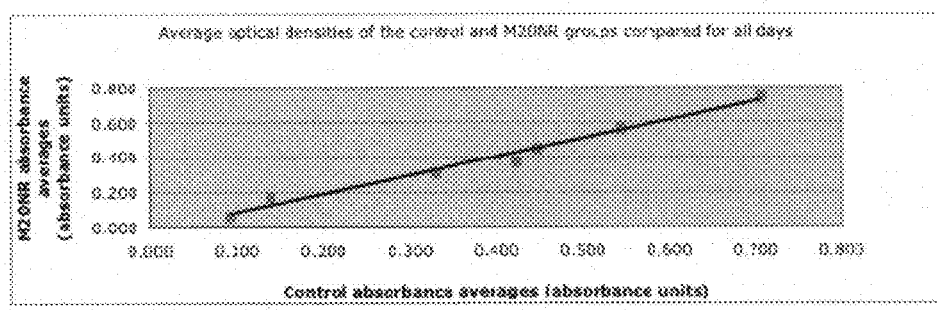

Figure 5. Scatter plot comparing corresponding average optical densities in the control and M20NR groups in all days. The best-fitting line gives the equation $y = 1.061x - 0.026$ and the $R^2$ value of 0.982.

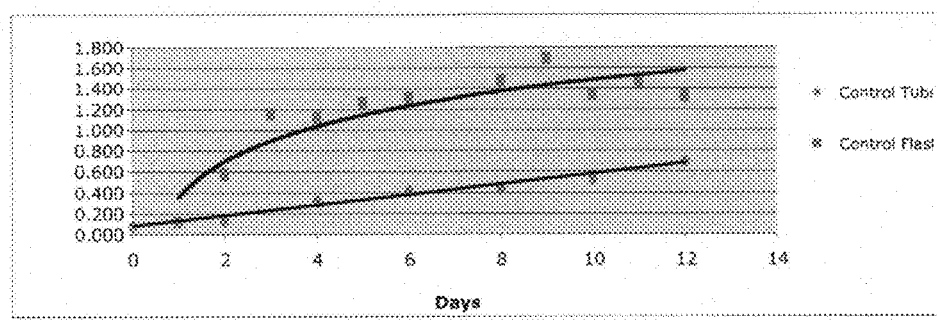

Figure 6. Average algal optical density in the control test tube group compared with optical density in the control flask over time. The average optical density in the control test tube group gives a best fitting line of $y = 0.0496x + 0.0855$ ($R^2 = 0.968$). A logarithmic regression model fit to the average optical density of the flask over time gives the equation $y = 0.489 \ln(x) + 0.3582$ ($R^2 = 0.810$).

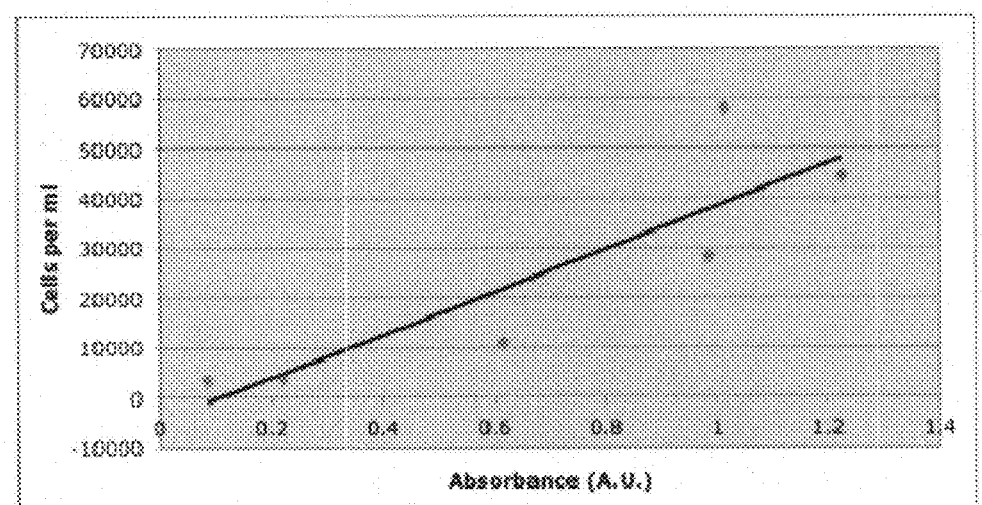
Figure 7. Calibration of algal optical density to cell density. This best-fitting line gives the equation y = 43090x - 4759. $R^2 = 0.766$.
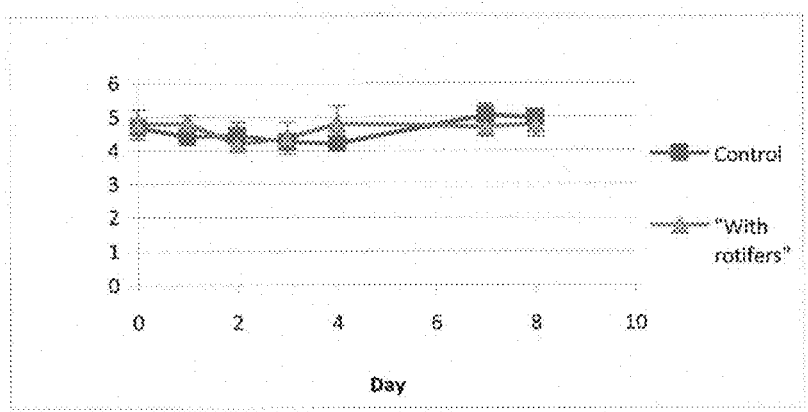
Figure 8. Dissolved oxygen levels in the control and rotifer groups during the test period. Y-axis error bars represent one standard deviation.

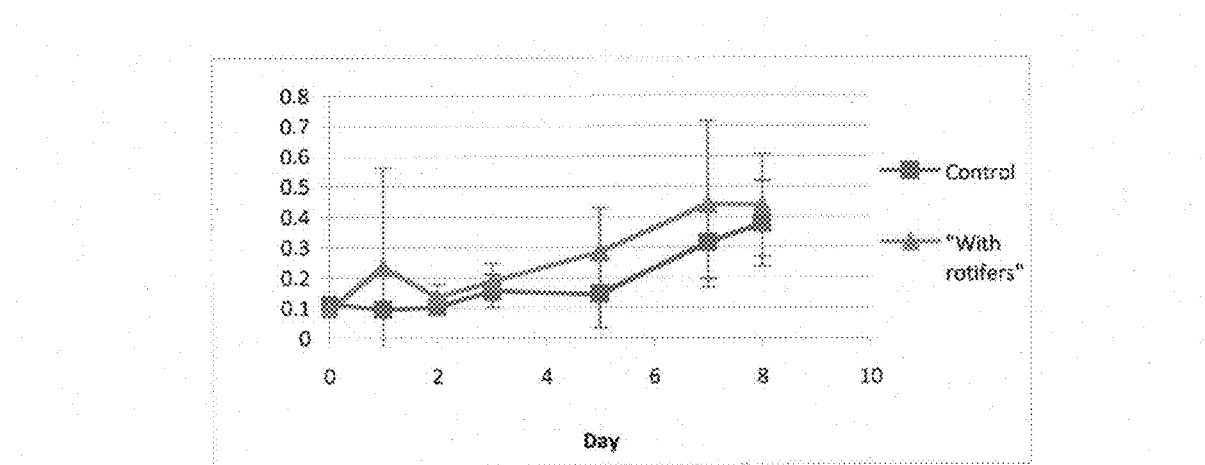
Figure 9. Optical density of the two algal groups during the test period. Y-axis error bars represent one standard deviation.

AQUACULTURE BIOCIDE METHODS AND COMPOSITIONS

CROSS-REFERENCE

This application claims the benefit of U.S. Provisional Application No. 61/384,292 filed Sep. 19, 2010, which is incorporated herein by reference.

BACKGROUND OF THE INVENTION

Algae cultivation has garnered much interest due to the wide variety of potential downstream products including food, fertilizer, bioplastics, dyes and colorants, chemical feedstock, pharmaceuticals, and biofuels. Additionally, algae cultivation has applications for pollution control.

Open pond systems are one system used for algae cultivation. The open pond system, however, exposes the algal crop to many relatively uncontrolled environmental factors, such as an increased risk of infestation by biological contaminants, including grazers. Grazers can be carried into open algal cultures by runoff water and windblown debris. Once in the algal solution, Grazers can multiply and consume the algal crop, sometimes ruining the entire culture.

Microscreens, zooplanktivorious fish, and pH/temperature shock methods have all been employed to combat grazer infestation in open ponds. Each of these methods has limitations. Screens have been found to be ineffective in removing the grazers, zooplanktivorious fish require food and would possibly compromise optimal growth conditions, and shocking cultures by regularly lowering or increasing pH or temperature for a short period requires large amount of chemicals or potentially expensive specialty apparatuses:

Methoprene is a relatively safe biocide. Methoprene rapidly degrades in sunlight and is practically non-toxic to humans or algae. The EPA does not consider methoprene application to result in unreasonable adverse effects on the environment.

SUMMARY OF THE INVENTION

The invention described herein is directed toward methods for controlling grazers in aquacultures using biocides. Compositions for controlling grazers in aquacultures are also described. The productions of products from algae grown while grazers are controlled using biocides are also described.

In some embodiments the method comprises:
a. growing algae in a media containing a biocide and an adjuvant, wherein the biocide and the adjuvant control a grazer population;
b. harvesting the algae;
c. producing a product from the harvested algae.

In some embodiments the product is agar, alginic acid, carrageenan, fuel, sugar, alkenes (olefins), lubricants, sulfur or sulfuric acid, bulk tar, asphalt, petroleum coke, paraffin wax, or aromatic petrochemicals.

In some embodiments the biocide is a synthetic hormone or hormone analogue.

In some embodiments the synthetic hormone or hormone analogue is methoprene.

In some embodiments the methoprene is added to the media to form a concentration of between 1 and 100 mg/L.

In some embodiments the biocide comprises a terpene.

In some embodiments the algae are genetically modified to produce the terpene.

In some embodiments the terpene is present in the media at between 500 ppm and 0.625 ppm.

In some embodiments the biocide is alpha-pinene.

In some embodiments the biocide comprises a limonoid.

In some embodiments the limonoid selected from the group consisting of limonin, nomilin, nomilinic acid, azadirachtin, cedrelanolide, toosendanin, ichangin, obacunone, 12,hydroxyamdorastatin, isofraxinellone, meliartenin, or a derivative of limonin, nomilin, nomilinic acid, azadirachtin, cedrelanolide, toosendanin, ichangin, obacunone, 12,hydroxyamdorastatin, meliartenin, or isofraxinellone.

In some embodiments the biocide comprises azadirachtin.

In some embodiments the adjuvant comprises acetone, propylene glycol, or nonylphenylethoxylate or a combination thereof.

In some embodiments the adjuvant comprises an anionic surfactant, a cationic surfactant, a non-ionic surfactant, an amphoteric surfactant or a combination thereof.

In some embodiments the anionic surfactant is selected from the group consisting of fatty acid sulphates, fatty acid ether sulphonates and their salts; alkyl aryl sulphonates, such as the sulphonate of dodecyl benzene, and their salts; fatty acid salts; mono, -di-, tri-aryl poly-glycolether phosphoric acid esters and their salts.

In some embodiments the cationic surfactant is selected from the group consisting of quatenary ammonium salt or a phenyl derivative thereof.

In some embodiments the non-ionic surfactant is selected from the group consisting of polyethoxylated castor oil, sorbitan, sorbitan esters, fatty alcohols, acids and esters, alkylphenols such as ethoxylated nonyl phenol, block polymers of ethylene and propylene oxide and their alkyl, aryl or alkylaryl condensates.

In some embodiments the amphoteric surfactant is alkyl betaine.

In some embodiments the algae is green algae, red algae, brown algae, golden-brown algae, blue-green algae (cyanobacteria), diatoms, or a combination thereof.

In some embodiments the algae is Amphipleura, Chlorella, Botryococcus, Dunaliella, Gracilaria, Nannochloris, Nannochlorpsis, Pleurochrysis carterae, Sargassum, Scendesmus, Spirulina, Ulva or a combination thereof.

In some embodiments the algae is a macroalgae, such as seaweed.

In some embodiments the grazers comprise rotifers, moina or a combination thereof.

In some embodiments the grazers comprise daphnia.

In some embodiments the grazers comprise tinnids.

In some embodiments the grazers comprise phytoplanktivorious ciliates.

In some embodiments the algae grown in the presence of a grazers grows to within 80-100% of a control algae absent grazers.

In some embodiments aquaculture medium for promoting algae growth comprising from about 0.01% to about 5% of biocide and 0.01% to about 5% of surfactant is described.

In some embodiments the biocide in the aquaculture medium comprises methoprene.

In some embodiments the biocide in the aquaculture medium comprises alpha-pinene.

In some embodiments the biocide in the aquaculture medium comprises azadirachtin.

In some embodiments the biocide in the aquaculture medium comprises resmethrin.

In some embodiments an open pond aquaculture system for producing biofuel comprising:
a. algae with a chlorophyll concentration of at least 300 µg/L
b. a biocide for controlling a grazer population c. an adjuvant for increasing the biocide's ability to control the grazer population.

In some embodiments an open pond aquaculture system for producing biofuel covers over at least 20 acres.

In one embodiment of the invention flocculation is instigated in algae to control grazer populations.

In one embodiment of the invention aquaculture media salinity is altered to control grazer populations.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 depicts algal optical density in experimental groups during a test period.

FIG. 4 depicts algal optical density in experimental groups without rotifers.

FIG. 5 depicts a scatter plot comparing corresponding average optical densities in the control and M20NR groups in all days. The best-fitting line gives the equation $y=1.061x-0.026$ and the R2 value of 0.982.

FIG. 6 depicts average algal optical density in a control test tube group compared with optical density in a control flask over time. The average optical density in the control test tube group gives a best fitting line of $y=0.0496x+0.0855$ ($R2=0.968$). A logarithmic regression model fit to the average optical density of the flask over time gives the equation $y=0.489 \text{Ln}(x)+0.3582$ ($R2=0.810$).

FIG. 7 depicts the calibration of algal optical density to cell density. This best-fitting line gives the equation $y=43090x-4759$. $R2=0.766$.

FIG. 8 depicts the dissolved oxygen levels in the control and rotifer groups during the test period. Y-axis error bars represent one standard deviation.

FIG. 9 depicts the optical density of the two algal groups during the test period. Y-axis error bars represent one standard deviation.

DEFINITIONS

Figure 1:
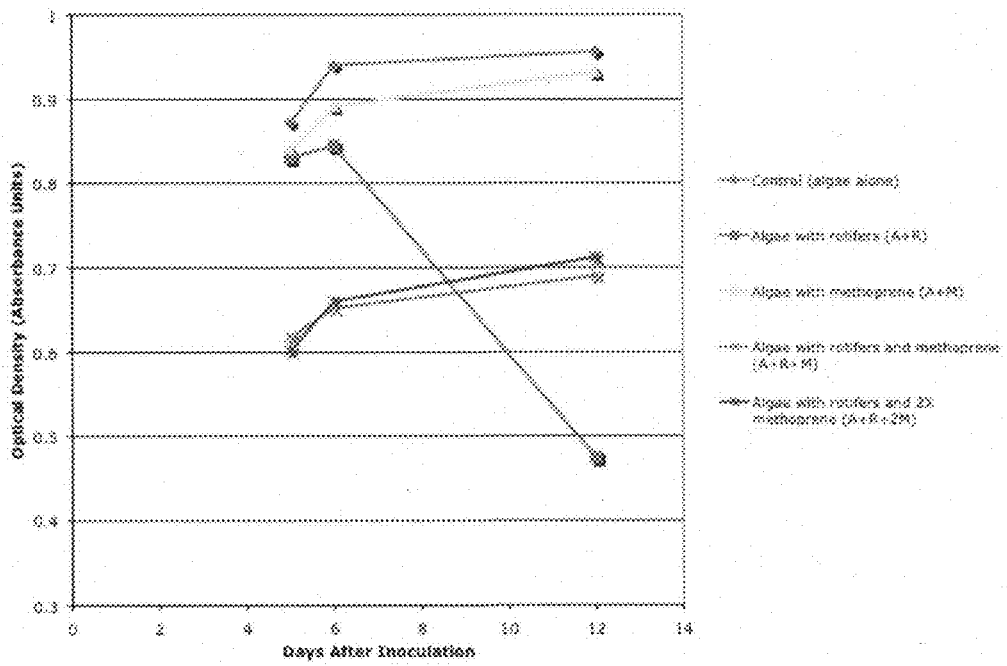
FIG. 1 depicts the mean optical density of the five test groups at 5, 6, and 12 days.

Unless defined otherwise, all technical and scientific terms used herein have the same meaning as commonly understood by a person of ordinary skill in the art. All values and numbers are understood to include acceptable tolerances and statistical ranges.

DETAILED DESCRIPTION OF THE INVENTION

The present invention is directed toward a method for controlling grazers in algae aquacultures using biocides. The biocide can be in the aquaculture media or added to the aquaculture media. Surfactants can be used in addition to biocides to control grazers. The biocide can be a synthetic hormone, a synthetic hormone analogue, a plant derived insecticide, a terpene or a combination thereof. As described further below algae can be cultured in the aquaculture with a reduction in algae loss due to grazers because the grazer population is controlled by the biocides. The algae can then be harvested, and a product, for instance biofuel, can be collected from or produced from the harvested algae.

The present invention is also directed toward a composition for promoting algae growth. The composition can comprise a biocide or a combination of biocides. The biocide can be a synthetic hormone, a synthetic hormone analogue, a plant derived insecticide, a terpene or a combination thereof. The composition can further comprise adjuvants such as surfactants.

The present invention is also directed toward monitoring the levels of biocides in an aquaculture. Absolute levels of biocide can be monitored in the aquaculture media, or in material surrounding the aquaculture media. Biocide levels can be monitored in relation to algae production. Biocide levels can be monitored in relation to grazer populations.

The present invention is also directed toward a system for the production of products from algae where the algae are grown at high concentrations in open pond aquacultures with biocides and adjuvants to control grazer populations.

Most importantly, the present invention is directed to methods of making a product, such as a fuel product or a pharmaceutical or nutriceutical product whereby the product is made by growing algae in an aquaculture comprising one or more biocides such as the ones described herein. Collecting a product from the aquaculture or algae, and optionally further processing it to make a final commercial product.

The various embodiments are described below in more detail.

I. AQUACULTURES

Aquaculture is any environment in which algae can grow. Aquacultures can use a media containing water. The aquacultures can use any media suitable for culturing algae. For instance, the media can be seawater, wastewater, fresh water, or buffered solutions.

The aquacultures herein preferably contain one or more biocide and optionally one or more adjuvants. Biocide and adjuvant can control grazers in any type of bioreactor suitable for aquaculture.

An aquaculture can be performed in closed bioreactors. The closed bioreactors can be photo-bioreactors. These bioreactors can have integrated sensors to detect the levels of biocides, to detect the levels of grazers, or to detect the levels of adjuvant. Such sensors would be useful to monitor when additional biocide is needed in the aquaculture. The bioreactors can also have integrated mechanisms for periodically adding biocides to the culture medium. The monitoring can be integrated with the ability to add biocide, providing for an automated process for controlling grazers.

An aquaculture can have sensors to detect the levels of biocides, to detect the levels of grazers, or to detect the levels of adjuvant. For example grazers can be detected by measuring metabolic waste products produced by grazers. Such sensors would be useful to monitor when additional biocide is needed in the aquaculture. The aquaculture can also have mechanisms for periodically adding biocides to the culture medium. The monitoring can be integrated with the ability to add biocide, providing for an automated process for controlling grazers.

The aquaculture media can be exposed to a biocide within a closed bioreactor. The media can also be exposed to a biocide prior to being added to a closed bioreactor. In some embodiments the media is cycled outside of the closed bioreactor to interact with a biocide and then returned to the closed bioreactor.

The aquaculture can also be an open pond system. The open pond system can be for instance a raceway pond. The open pond can be equipped to cause motion of the algae. For instance the motion can be caused by paddles or wheels. The equipment that causes motion of the algae can contain biocides that are released into the media over time. The biocide releasing and motion causing equipment can be replaced as necessary to maintain proper biocide levels.

The open ponds can be lined with clay, asphalt, PVC or other material that prevents runoff or loss or media. In some aspects biocides are found in the lining of the open pond. The lining of the open pond can be engineered to release biocide into the aquaculture over time. For instance a pond could be coated with compositions described herein to release biocide over time. The ponds can periodically be re-coated to provide for continued biocide release.

Typically open pond aquacultures are located on land; however in some embodiments the open pond systems are located on the surface of the ocean or other body of water. In some embodiments the open ponds are ponds that float on the surface of the ocean or other body of water. For instance large rafts, covering tens of acres of aquacultures, can float on the sea and grow algae in the presence of biocides and adjuvant to control grazers. The algae, which are produced at a high level due in part to any grazers being controlled by the biocides and the adjuvants, can be collected and products can be produced.

The aquaculture can be located on a body of water. In some embodiments the aquaculture is a region on a body of water seeded with algae for later collection. The biocide can be added to an aquaculture on a body of water to control grazers. In large aquacultures biocide can be added by boat, by airplane, or by terrestrial sprayers. In some aspects buoys containing biocide provide biocide to the aquaculture.

In some aspects biocide is delivered to an aquaculture on a body of water by embedding the biocides in compositions that degrade in water over time releasing the biocide at a controlled rate. In some embodiments biocides are released at intervals from stores of biocide located within the aquaculture.

The aquaculture can be an Integrated Multi-Trophic Aquaculture. In some embodiments the aquaculture is Integrated Aquaculture.

The aquacultures, including open pond aquacultures, can be located to in regions that minimize the risk that the activities have on non-target organisms. For example, the aquacultures can be located in the desert far from sensitive species. Additionally the aquacultures could be located in a region where any organisms would periodically freeze.

There are various examples of aquaculture techniques that can all be used in the present invention. For example U.S. Pat. No. 7,717,065 describes an improved aquaculture system. Grazers can be controlled in such a system using the methods and compositions of the present invention.

The aquaculture media can be brackish. In some embodiments of the in invention the salinity of the media is altered for periods of time to control the grazer population. For example, the salinity can be changed in a pulsed fashion, e.g., an increase of salinity can be made every for example hour, 6 hrs, day, 3 days. The salinity can be altered for minutes, hours or days. The algae are tolerant to the salinity changes that control the grazer populations. The salinity during the alteration period can be increased up to 0.05%, 0.5%, 5%, 10%, 20%, 30%, 40%, 50%, or 60%.

II. ALGAE

The present invention involves the culturing of algae. It is recognized that there are many kinds of algae and the present invention is not limited by kind. Any algae that can be the target of grazers will benefit from the addition of the biocides and adjuvants presently described. In some instances, a combination of algae can be grown in a single aquaculture.

In some embodiments the algae are microalgae. However, the algae can also be macroalgae. The algae can be green algae, red algae, brown algae, golden-brown algae, blue-green algae (cyanobacteria), diatoms, or a combination thereof. In some applications of the invention algae are *Amphipleura, Chlorella, Botryococcus, Dunaliella, Gracilaria, Nannochloris, Nannochlorpsis, Pleurochrysis carterae, Sargassum, Scendesmus, Spirulina, Ulva* or a combination thereof. Thus, the present invention contemplates an aquaculture comprising any one or more of the above algae in combination with one or more biocides.

The algae of the invention can also be subjected to artificial selection or be genetically-modified algae. In some instances the algae are subjected to a chemical or radiation to cause a mutation while in the presence of a selection agent. The algae can be selected for high lipid content, for instance the algae can be blue-green algae selected for high lipid. These algae can then be cultured in the presence of a biocide and a adjuvant to control any grazers present in the culture.

The levels of algae in an aquaculture are important to measure to understand the state of the aquaculture. The levels can be measured by any means known in the art, including measuring the algal biomass by chlorophyll concentration using spectrophotometric and fluorometric techniques. Chlorophyll ratios can indicate different populations of algae present.

The algae can be genetically modified. Sometimes the genetic modification is related to the present invention, but it is recognized that an algae with any genetic modification may benefit from controlling grazers. In some embodiments the algae are genetically modified to produce a biocide. In some embodiments the algae are selected to be resistant to a biocide. In some embodiments the algae are genetically modified to be resistant to the biocide. Expression Vectors and Host Cell Transformation can be done as previously described, for instance as in US 2009/01262260 or US 2009/0246766.

In some embodiments algae genetically modified to produce a biocide are combined in an aquaculture with algae selected to produce products.

Constructs and methods to engineer thermophilic cyanobacteria have been previously described, for instance in US 2011/0020867. The previously contemplated constructs can be used to produce biocides for controlling grazers in aquacultures. The previously contemplated methods can further comprise use of a biocide to control grazers in combination with an adjuvant.

The invention can be applied to control grazers in algae that have been modified for other purposes. For instance, hyperphotosynthetic organisms have been described in U.S. Pat. No. 7,785,861. In some embodiments the algae of the present invention are hyperphotosynthetic organisms which are grown in an aquaculture in the presence of a biocide and an adjuvant to control the grazer population. Additionally, U.S.

Pat. No. 7,794,969, U.S. Pat. No. 7,851,188, US 2011/0015417, US 2009/0155869, US 2009/0246842, US 2008/0293125, and US 2011/0020883 and US 20110045592 describe more examples of modified organisms which could be cultivated in the presence of a biocide and an adjuvant to control grazers.

III. BIOCIDES FOR THE CONTROL OF GRAZERS

Controlling the populations of grazers in aquacultures is contemplated by the invention. Grazers can be any organism that consumes algae. In some embodiments the grazers are rotifers, cladocera, or copepods. In some embodiments the cladocera are daphnia. In some embodiments the grazers are baetids.

Controlling the grazer population can achieved by preventing grazers from becoming established in an aquaculture, by killing the grazers, or by inhibiting the grazers ability to reproduce. In some aspects controlling the grazer population is achieved by altering the male to female ratio. In some aspects controlling the grazer population is achieved by inhibiting an important grazer function such as feeding. In some aspects the addition of a biocide results in a decrease in the incidence of male grazer broods and in increase in the incidence of all female grazer broods.

In some embodiments controlling the grazer population is achieved by limiting the size of a population of grazers in an aquaculture relative to the size of a grazer population in a control aquaculture wherein the control aquaculture is absent biocide. In some aspects the grazer population is limited to less than 10%, 20%, 30%, 40%, 50%, 60%, 70%, 80% or 90% of the grazer population in a control aquaculture.

In some embodiments controlling the grazer population is achieved by reducing the number of grazers in an aquaculture. In some aspects the reduction of grazers is at least a 10%, 20%, 30%, 40%, 50%, 60%, 70%, 80% or 90% reduction of grazers after treatment with a biocide (e.g., after 6 hrs, 1 day or 2 days).

In some instances, the addition of a biocide maintains light penetration in the pond for at least 6 inches, 1 ft, 2 ft, 3 ft, 4 ft, 5 ft, 6 ft, or more.

In some instances, the biocide provides that the aquaculture is maintained at an optical density of 0.95 or higher, 0.9 or higher, 0.8 or higher, 0.7 or higher or 0.6 or higher for example, for a day, 2 days, 3 days, 4, days, 5 days, 6 days, a week, a month, or for unlimited periods of time.

In some instances, an aquaculture comprises an inlet for continuous or sporadic input of one or more biocides. The inlet can be connected to a reservoir comprising the biocide(s).

In some instances, the biocides herein maintain an optical density of less than 0.9, 0.8, or 0.7 AU in the aquaculture. Thus the present invention provides for a method for generating a product by growing an algae culture at an optical density of less than 0.8 AU for a period of time to product a product, collecting the product from the algae or algae culture and optionally further refining it.

Various embodiments involve the use of biocides to control the grazer population in aquacultures. The biocides control the grazer population. Some biocides have increased efficacy with the addition of an adjuvant. The adjuvant can, for instance, increase the solubility of the biocide, or increase the ability of the biocide to enter the grazer.

A biocide can be a synthetic hormone or hormone analogue. In some aspects the synthetic hormone or hormone analogue is juvenile hormone or juvenile hormone analogue.

In some aspects the synthetic hormone or hormone analogue is methoprene or a derivative thereof. In some aspects the methoprene is S-methoprene. In some aspects the synthetic hormone or hormone analogue is ecdysone, vitellogenin, or a derivative of ecdysone or vitellogenin. In some aspects the synthetic hormone or hormone analogue is Methyl farnesoate, Juvenile hormone 0, Juvenile hormone I, Juvenile hormone II, Juvenile hormone III, or Juvenile hormone JHB3. In some aspects the synthetic hormone or hormone analogue is a derivative of Methyl farnesoate, Juvenile hormone 0, Juvenile hormone I, Juvenile hormone II, Juvenile hormone III, or Juvenile hormone JHB3. In some aspects the synthetic hormone or hormone analogue is ecdysis-triggering hormone, eclosion hormone, crustacean cardioactive peptide, or trypsin-modulating oostatic factor.

In some aspects synthetic hormone or hormone analogue is added to an aquaculture as a granule with 1.5% active ingredient (a.i.), briquette (2.1% a.i.), pellet (4.25% a.i.), or liquid (20% a.i.). In some embodiments the synthetic hormone or hormone analogue granules use range from 5.6 to 22.4 kg/ha water surface area. In some embodiments the synthetic hormone or hormone analogue granules use range from 2.5 mL per 32 sq ft to 500 mL per 3200 sq ft water surface area. In some embodiments pellet application rates range from 2.8 to 11.2 kg/ha. In some embodiments liquid synthetic hormone or hormone analogue application rates are 73 mL/ha. It is appreciated that application rates depend on such factors as the target grazer species, water depth, vegetation cover, size of the aquaculture, as well as the presence/absence of aquatic pollution. In some embodiments the concentration of synthetic hormone or hormone analogue added to the aquaculture is up to 1000 µg/L, up to 300 µg/L, up to 100 µg/L, up to 10 µg/L, up to 1 µg/L, up to 0.1 µg/L, or up to 0.01 µg/L. In some embodiments the concentration of synthetic hormone or hormone analogue added to the aquaculture is at least 1000 µg/L, at least 300 µg/L, at least 100 µg/L, at least 10 µg/L, at least 1 µg/L, at least 0.1 µg/L, or at least 0.01 µg/L.

In some embodiments the method comprises the addition of a solid shelf-life extending pesticide formulation to an algae aquaculture containing an adjuvant for the production of biofuels, wherein the pesticide formulation consisting of: a) methoprene on a solid carrier, wherein said solid carrier is selected from the group consisting of dry molasses and silica gel; b) molasses as a shelf-life extending agent, wherein said solid formulation is formulated as a feed-through animal product wherein the ratio of said molasses to said methoprene is about 100,000:1 w/w to about 500:1 w/w, wherein said final form is about 1 kilogram to 250 kilograms in size; c) an antioxidant; d) a mineral; and e) optionally a protein (similar to the method described in U.S. Pat. No. 7,348,019). In some aspects the methoprene on a solid carrier is shaped into a form that will attach to an open pond aquaculture. In some aspects the methoprene on a solid carrier is shaped into a form that will interact with the media in an open pond aquaculture. In some aspects the methoprene on a solid carrier is shaped into a paddle or component or attachment to a paddle for causing motion in an open pond aquaculture. In some aspects the methoprene on a solid carrier is shaped into a buoy for use an open pond aquaculture.

In some embodiments the biocide is produced by genetically modified algae. In some aspects the genetically modified algae produce a synthetic hormone or hormone analogue.

The biocide can be a plant derived insecticide. Examples of a plant derived insecticides include Anabasine, Anethole, Annonin, Asimina, Azadirachtin, Caffeine, *Carapa*, Cinnamaldehyde, Cinnamon leaf oil, Cinnamyl acetate, Deguelin, Derris (rotenone), *Desmodium caudatum*, Eugenol, Linalool, Myristici Neem (Azadirachtin), *Nicotiana rustica* (nicotine), *Peganum harmala*, Oregano oil, Polyketide, Pyrethrum, Quassia, Tetranortriterpenoid, or Thymol. In some aspects the plant derived insecticide is a derivative of Anabasine, Anethole, Annonin, Asimina, Azadirachtin, Caffeine, *Carapa*, Cinnamaldehyde, Cinnamon leaf oil, Cinnamyl acetate, Deguelin, Derris (rotenone), *Desmodium caudatum*, Eugenol, Linalool, Myristicin, Neem (Azadirachtin), *Nicotiana rustica* (nicotine), *Peganum harmala*, Oregano oil, Polyketide, Pyrethrum, Quassia, Tetranortriterpenoid, or Thymol.

The biocide can be a terpene. In some aspects a terpene is provided to an open pond aquaculture via conifers planted in close proximity to the open ponds. In some aspects a terpene is provided to an open pond aquaculture via eucalyptus planted in close proximity to the open ponds. In some embodiments algae are genetically modified to produce a terpene.

In some embodiments the biocide is alpha-pinene. In some embodiments the biocide is a Hemiterpene, Monoterpene, Sesquiterpene, Diterpene, Sesterterpene, Triterpene, Tetraterpene, or Polyterpene. In some embodiments the biocide is nodulisporic acid A, nodulisporic acid $A_1$ or nodulisporic acid $A_2$.

In some embodiments the terpene is a terpenoid. In some embodiments the biocide comprises a limonoid.

In some embodiments the limonoid selected from the group consisting of limonin, nomilin, nomilinic acid, azadirachtin, cedrelanolide, toosendanin, ichangin, obacunone, 12,hydroxyamdorastatin, isofraxinellone, meliartenin, or a derivative of limonin, nomilin, nomilinic acid, azadirachtin, cedrelanolide, toosendanin, ichangin, obacunone, 12,hydroxyamdorastatin, meliartenin, or isofraxinellone.

The biocide can be the pyrethroid resmethrin.

The biocide can be added periodically. For instance the biocide can be added hourly, daily, or weekly. The biocide can be added when there is an attack by grazers. The biocide can be added when a measurement that reflects an increase in grazers is detected. In one embodiment biocide is added in response to a change in the algal turbidity measurement in an aquaculture. In another embodiment the biocide is added after a change in the dissolved oxygen content of the aquaculture.

In some embodiments the biocide is a combination of biocides described herein. In some embodiments the biocide is a cocktail of two or more biocides. In some embodiments the biocides in the cocktail are synergistic. In some embodiments the cocktail is a multi-pesticide emulsion.

Other examples of biocides include those described in US 20090082409.

In some embodiments the biocide is added to an aquaculture as a liquid. In some embodiments the biocide is added to an aquaculture as a solid. In some embodiments the biocide is added to an aquaculture in a gas that is bubbled through the aquaculture solution. In some embodiments the biocide is embedded in a solid that will dissolve slowly to release the biocide over time. In some aspects while embedded in the solid the biocide is protected from degradation.

In some embodiments the biocide has the property of low toxicity. In some aspects the biocide is not toxic to algae; but is effective in controlling the grazer population. In some aspects the biocide is not toxic to humans at a concentration of $\leq 1.0$ mg/L, $\leq 10$ mg/L, or $\leq 100$ mg/L with acute exposure. In some aspects the biocide is not toxic to humans at a concentration of $\leq 1.0$ mg/L, $\leq 10$ mg/L, or $\leq 100$ mg/L with chronic exposure. In some embodiments the biocide exhibits a very low toxicity to mammals (for instance the LD50 in rats is >3,540 mg/kg making it practically non-toxic).

In some embodiments the biocide is biodegradable. For example, it might biodegrade within 50, 100, or 150 hours when exposed to light and/or non-sterile water.

In some embodiments, an aquaculture is provided with one or more biocide for a final concentration of up to 1000 mg/L, 100 mg/L, 10 mg/L, 1 mg/L, 0.1 mg/L, 0.01 mg/L, 1000 µg/L, 100 µg/L, 10 µg/L, 1 µg/L, 0.1 µg/L, or 0.01 µg/L. In some embodiments, an aquaculture is provided with one or more biocide for a final concentration of greater than 1000 mg/L, 100 mg/L, 10 mg/L, 1 mg/L, 0.1 mg/L, 0.01 mg/L, 1000 µg/L, 100 µg/L, 10 µg/L, 1 µg/L, 0.1 µg/L, or 0.01 µg/L.

In some aspects biocide is added to an aquaculture as a granule with 1.5% active ingredient (or a.i.), briquette (2.1% a.i.), pellet (4.25% a.i.), or liquid (20% a.i.). In some embodiments the biocide granules use range from 5.6 to 22.4 kg/ha water surface area. In some embodiments the biocide granules use range from 2.5 mL per 32 sq ft to 500 mL per 3200 sq ft water surface area. In some embodiments pellet application rates range from 2.8 to 11.2 kg/ha. In some embodiments liquid larvicide application rates are 73 mL/ha. It is appreciated that application rates depend on such factors as the target grazer species, water depth, vegetation cover, size of the aquaculture, as well as the presence/absence of aquatic pollution.

In some embodiments the concentration of biocide in an aquaculture is maintained at a concentration of up to 1000 mg/L, 100 mg/L, 10 mg/L, 1 mg/L, 0.1 mg/L, 0.01 mg/L, 1000 µg/L, 100 µg/L, 10 µg/L, 1 µL, 0.1 µg/L, or 0.01 µg/L. In some embodiments, the concentration of biocide in an aquaculture is maintained at a rate of greater than 1000 mg/L, 100 mg/L, 10 mg/L, 1 mg/L, 0.1 mg/L, 0.01 mg/L, 1000 µg/L, 100 µg/L, 10 µg/L, 1 µg/L, 0.1 µg/L, or 0.01 µg/L.

The biocide can be a plant derived insecticide, a terpene, or a terpenoid or, a limnoid.

In some embodiments the biocide is present in the aquaculture media at between 0.01 and 500 ppm or more preferably between 1 and 400 ppm or more preferably between 50 and 100 ppm.

In some embodiments bacteria are introduced into the aquaculature to produce biocides. The bacteria can form a biofilm that is genetically modified to produce biocides. The biofilm can be a phototropic biofilm. The biofilm can be adhered to the walls of a open pond or adhered to a solid structure introduced to support the biofilm. The biofilm can also be adhered to equipment that is necessary for the aquaculture and was not particularly designed for a biofuel. The biofilm can comprise *E. coli* genetically modified to produce a biocide. In some aspects a biofilm comprising *E. coli* is genetically modified to produce a hormone or hormone analog is adhered to the walls of an open pond aquaculture. In some aspects a biofilm comprising *E. coli* is genetically modified to produce methoprene, azadirachtin, or alpha-pinene is adhered to the walls of an open pond aquaculture.

Thus in some instances, the present invention contemplates culturing algae in an aquaculture wherein said aquaculture comprises a biocide at a concentration of between 0.01-500 ppm or greater than 10 mg/L, or such that the aquaculture has an optical density of less than 0.9 AU and harvesting from said algae culture a compound that can be further processed into a commercial products.

In some embodiments, the biocide is one that allows algae to continue to grow at day 5-12 after administration of the biocide to the aquaculture.

Sometimes, in addition to controlling algae, the biocides can aid the growth of algae. For instance algae grown in the presence of a biocide will have a growth rate greater than the growth rate of algae grown when the biocide is present. This beneficial feature can in some embodiments occur in the absence of grazers. The growth rate of the algae can be increased by addition of a biocide by at least 0.05%, 0.5%, 1%, 5%, 10%, or 25%.

IV. ADJUVANTS

Various embodiments of the invention involve the use of adjuvants in increase the ability of a biocide to control a grazer population. The adjuvants can comprise surfactants, emulsifiers, carriers, or solvents. The adjuvant concentrations can be selected to not significantly inhibit algal growth. The adjuvant can be added simultaneously with or at different times than the biocide to the aquaculture.

A surfactant can be used in addition to a biocide. Sometimes the surfactant and the biocide are premixed in a solution ready to be delivered to an aquaculture.

In some embodiments the adjuvant is acetone. Acetone can added to the aquaculture media at a concentration of between 1 and 27 ml/L. In some aspects acetone is added to the aquaculture media at a concentration of 0.1, 1, 5, 10, 20, 30, 40, 50, or 60 ml/L.

In some embodiments the surfactant comprises an anionic surfactant, a cationic surfactant, a non-ionic surfactant, an amphoteric surfactant or a combination thereof. In some aspects the anionic surfactant is selected from the group consisting of fatty acid sulphates, fatty acid ether sulphonates and their salts; alkyl aryl sulphonates, such as the sulphonate of dodecyl benzene, and their salts; fatty acid salts; mono,-di-, tri-aryl poly-glycolether phosphoric acid esters and their salts. In some aspects the cationic surfactant is selected from the group consisting of quaternary ammonium salt or a phenyl derivative thereof. In some aspects the non-ionic surfactant is selected from the group consisting of polyethoxylated castor oil, sorbitan, sorbitan esters, fatty alcohols, acids and esters, alkylphenols such as ethoxylated nonyl phenol, block polymers of ethylene and propylene oxide and their alkyl, aryl or alkylaryl condensates. In some aspects the amphoteric surfactant is alkyl betaine.

In some embodiments the adjuvant is propylene glycol. In some aspects propylene glycol is added to the aquaculture media at a concentration of at least 1, 5, 10, 20, 30, 40, 50, or 60 ml/L or less than 200, 100, 50, 30, or 20 mg/L.

In some embodiments the adjuvant is nonylphenylethoxylate. In some aspects nonylphenylethoxylate is added to the aquaculture media at a concentration of at least 1, 5, 10, 20, 30, 40, 50, or 60 ml/L or less than 200, 100, 50, 30, or 20 mg/L.

V. HARVESTING

Once the algae is grown under conditions that control grazers it is harvested to make a product. Non-limiting examples of harvesting techniques include flocculation, froth floatation, microscreening and centrifugation. In some aspects froth floatation is suspended air floatation or dispersed air flotation.

The algae can be harvested selectively, wherein organisms modified to produce biocides are not harvested. For instance floating algae are harvested and a biofilm that is producing a biocide is left in the aquaculture. The algae can be continuously harvested or harvested in batches.

VI. PRODUCTS

A product can be produced from the harvested algae. Non-limiting examples of products which can be produced include agar, alginic acid, carrageenan, fuels, alkenes (olefins), lubricants, sulfur or sulfuric acid, bulk tar, asphalt, petroleum coke, paraffin wax, and aromatic petrochemicals. Additional products including food, fertilizer, bioplastics, dyes and colorants, chemical feedstock, pharmaceuticals, nutriceuticals, and biofuels. One other interesting end product is sugar. An algae farmer could potentially harvest some high polysaccharide algae, for instance *Chlorella*, and use the sugar as a feedstock for modified yeast that make anything from gasoline to cotton to antimalarial drugs. A specific example would be to use sugar derived from algae grown in the presence of biocides and adjuvant to control grazer populations to feed the organisms described in US 2010/0136641 to produce butanol.

Numerous methods for the large scale production of biofuels exist. The present invention can be an additional step in the previously described process or an additional step performed at a described facility. For instance US 2010/0297749 describes methods and systems for biofuel productions. In some embodiments the present invention comprises the methods and systems of US 2010/0297749 or 20100064573 further comprising the addition of biocides and adjuvants to control grazer populations. Similarly the methods of U.S. Pat. No. 7,883,882 can further comprise the inclusion of biocides and adjucants to control the grazer populations.

Refining hydrocarbons has been previously described and methods for improving refining techniques are the subject of pending patent applications, for instance US 2009/01262260. The present invention can be used as additional steps to reduce grazer populations in the previously described techniques. In some embodiments the biocide is a terpene that is present at a level suitable for controlling a grazer population, but not suitable for refining. In some embodiments the biocide is a terpene that is present at a level suitable for controlling a grazer population, but not suitable for producing insecticide as a product.

Examples of fuel products include small alkanes (for example, 1 to approximately 4 carbons) such as methane, ethane, propane, or butane, which may be used for heating (such as in cooking) or making plastics. Fuel products may also include molecules with a carbon backbone of approximately 5 to approximately 9 carbon atoms, such as naptha or ligroin, or their precursors. Other fuel products may be about 5 to about 12 carbon atoms or cycloalkanes used as gasoline or motor fuel. Molecules and aromatics of approximately 10 to approximately 18 carbons, such as kerosene, or its precursors, may also be fuel products. Fuel products may also include molecules, or their precursors, with more than 12 carbons, such as used for lubricating oil. Other fuel products include heavy gas or fuel oil, or their precursors, typically containing alkanes, cycloalkanes, and aromatics of approximately 20 to approximately 70 carbons. Fuel products also includes other residuals that can be derived from or found in crude oil, such as coke, asphalt, tar, and waxes, generally containing multiple rings with about 70 or more carbons, and their precursors.

The various fuel products may be further refined to a final product for an end user by a number of processes. Refining can occur by fractional distillation. For example, a mixture of fuel products, such as a mix of different hydrocarbons with different various chain lengths may be separated into various components by fractional distillation.

Refining may also include any one or more of the following steps; cracking, unifying, or altering the fuel product. Large fuel products, such as large hydrocarbons (e.g. .gtoreq.C10), may be broken down into smaller fragments by cracking.

Cracking may be performed by heat or high pressure, such as by steam, visbreaking, or coking. Fuel products may also be refined by visbreaking, for example reducing the viscosity of heavy oils. Refining may also include coking, wherein a heavy, almost pure carbon residue is produced. Cracking may also be performed by catalytic means to enhance the rate of the cracking reaction by using catalysts such as, but not limited to, zeolite, aluminum hydrosilicate, bauxite, or silica-alumina. Catalysis may be by fluid catalytic cracking, whereby a hot catalyst, such as zeolite, is used to catalyze cracking reactions. Catalysis may also be performed by hydrocracking, where lower temperatures are generally used in comparison to fluid catalytic cracking. Hydrocracking typically occurs in the presence of elevated partial pressure of hydrogen gas. Fuel products may be refined by catalytic cracking to generate diesel, gasoline, and/or kerosene.

The fuel products may also be refined by combining them in a unification step, for example by using catalysts, such as platinum or a platinum-rhenium mix. The unification process typically produces hydrogen gas, a by-product which may be used in cracking.

The fuel products may also be refined by altering or rearranging or restructuring hydrocarbons into smaller molecules. There are a number of chemical reactions that occur in the catalytic reforming process of which are known to one of ordinary skill in the arts. Generally, catalytic reforming is performed in the presence of a catalyst and high partial pressure of hydrogen. One common process is alkylation. For example, propylene and butylene are mixed with a catalyst such as hydrofluoric acid or sulfuric acid.

The fuel products may also be blended or combined into mixtures to obtain an end product. For example, the fuel products may be blended to form gasoline of various grades, gasoline with or without additives, lubricating oils of various weights and grades, kerosene of various grades, jet fuel, diesel fuel, heating oil, and chemicals for making plastics and other polymers. Compositions of the fuel products described herein may be combined or blended with fuel products produced by other means.

Some fuel products produced from the host cells of the invention, especially after refining, will be identical to existing petrochemicals, i.e. same structure. Some of the fuel products may not be the same as existing petrochemicals. However, although a molecule may not exist in conventional petrochemicals or refining, it may still be useful in these industries. For example, a hydrocarbon could be produced that is in the boiling point range of gasoline, and that could be used as gasoline or an additive, even though it does not normally occur in gasoline.

VII. TESTING

Testing and measurements can be performed to insure that grazers are being controlled. The levels of biocides or grazers can be determined at a single time or at different time points. The levels of biocides can also be determined at different distances from an open pool aquaculture. In some aspects the testing is done by automated processes.

The levels of biocides in an open pond lining can also be detected, for instance by obtaining a sample from an open pond lining and detecting the levels of biocide. The method can further comprise obtaining samples from multiple distances from the open pond and comparing the biocide levels. In some embodiments the levels of biocides detected in the open pond lining are used to direct the levels of biocides present in the aquaculture media.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

VIII. EXAMPLES

Example 1

Materials

Organisms

The *Chlorella* sp. used in this project was purchased from Carolina Biological Supply Company and received in a 20-mL solution of algae and Alga-Gro® Freshwater Medium. The *Brachionus* sp. rotifers used in this study were purchased from Ward's Natural Science.

Medium

For culturing and expanding the *Chlorella* to test volume and density, a modified Bristol medium (Bold, 1949) was used. This medium was composed of the following components per liter of distilled water: 0.02 g $(NH_4)_2HPO$ obtained from Mallinckrodt, St Louis, Mo.; 0.25 g $NaNO_3$ from Nurnberg Scientific, Portland Oreg.; 0.025 g 93% $CaCl_2.2H_2O$ from Alpha Aesar, Ward Hill, Mass.; 0.075 g $MgSO_4.7H_2O$ from J. T. Baker Chemical Co., Phillipsburg, N.J.; 0.075 g $K_2HPO_4$ from American Scientific; 0.175 g $KH_2PO_4$ from Mallinckrodt; and 0.025 g NaCl from Oregon Episcopal School. Based on the findings of Liang et al. (2009), ten grams of glucose per liter of water were also included to increase algal growth rates. Reagent grade glucose was obtained from Flinn Scientific, Batavia, Ill.

During the twelve-day test period, algae and rotifers were not cultured in pure modified Bristol medium, but were instead cultured largely in 20% artificial seawater, the base solution utilized by Ahmad et al. (2007). An undiluted concentration of this artificial seawater was made from mixing one cup (325 mL) of Instant Ocean powder into one gallon (3.78 liters) of distilled water.

Test Conditions

During the twelve-day test period, *Chlorella* and rotifers were cultured in 40-oz mason jars (Kerr, Avalon, Ball) within an algae-growing apparatus supplied by Oregon Episcopal School. The mason jars were illuminated by two 40-W 12-ft General Electric Plant Aquarium EcoBulb fluorescent light bulbs and two 40-W 12-ft Phillips Natural Sunshine fluorescent bulbs. The photoperiod was regulated by an electric timer. Some algae and rotifers were exposed to methoprene. Analytical grade methoprene was purchased from Sigma (St. Louis, Mo.). Water temperature was measured with a mercury thermometer. pH was determined with a Vernier pH probe. Specific gravity was determined with an Instant Ocean specific gravity measurement device.

Instrumentation

Optical density measurements were taken using a Fisher Scientific Spectro Master model 410 spectrometer. Algal samples were centrifuged in a combination centrifuge model L-708 (The Drucker Co.). Samples were homogenized by a Fisher Scientific model 232 Touch Mixer. A Fisher EMD XE series model 100A electronic balance scale was employed for weighing out Nile red. Fluorimetric measurements were taken with the Sargent-Welch ChemAnal system. Rotifers were counted with a Swift microscope and a Wolfe stereoscopic microscope.

Fluorescence

Standard Fluka Nile red was purchased from Sigma. Acetone was obtained from Oregon Episcopal School.

Methods:

Culture and Expansion to Necessary Volume 5 mL *Chlorella* sp. in Alga-Gro® Freshwater Medium (Carolina) were expanded into a total of 15 mL by means of addition of sterile modified Bristol Medium. Over the course of 29 days, these 15 mL were cultured and expanded into 2.5 liters in modified Bristol Medium kept in a 1-gallon container.

Preparation of *Brachionus* Solution

One day prior to the general test period, the rotifer concentration was determined. The rotifer concentration of the bottle was estimated by counting rotifers in three trials of 30-µL samples with a Swift microscope at 1.25× magnification. Rotifer concentration was estimated again with the same procedure on the day of inoculation.

Test Culturing

Algae were expanded into 500 ml of 20% artificial seawater in mason jars and subjected to five treatment conditions. Five replicates were conducted for each of the conditions. The test conditions were: control (algae only), rotifers without methoprene (A+R), methoprene without rotifers (A+M) methoprene with rotifers (A+R+M), and double concentration methoprene with rotifers (A+R+2M). In the mason jars containing solutions "with rotifers", 9 mL of media were replaced with rotifer solution. In the A+M and A+R+M groups, the solution was modified to give a methoprene concentration of 30 mg/L. In the A+R+2M group, the solution was modified to give a methoprene concentration of 62 mg/L.

During the test period, algae was kept on a 12-hour light: 12-hour dark photoperiod at 26.8° C. The pH and specific gravity of the 20% artificial seawater solution were measured to be 8.92±0.02 and 1.013 respectively.

Optical Density

Optical density measurements were taken on days 5, 6, and 12 after inoculation. Each jar was first agitated either by gently rocking back and forth until minimal algal residue could be seen on the bottom. Occasionally, a sterile tube or pipette was employed to scrape some residue into the solution. Once minimal algal residue remained in the jar, a 5-mL sample of solution was pipetted out with a sterile pipette. The sample's optical density was read with a spectrometer at 680 nm. Control and A+R sample readings were blanked with a solution of 10 mL modified Bristol medium per 40 mL 20% artificial seawater. A+M and A+R+M sample readings were blanked with a solution of 10 mL modified Bristol medium per 38.5 mL 20% artificial seawater and 1.5 mL methoprene-seawater solution. A+R+2M sample readings were blanked with a solution of 10 mL modified Bristol medium per 36.9 mL 20% artificial seawater and 3.1 mL methoprene-seawater solution. Optical density readings were taken in absorbance units.

Rotifer Count 12 days after inoculation a 5-mL sample was extracted from each of the 15 jars containing rotifer solution. 24 hours after extraction, these samples were examined with microscopy. From each of the fifteen 5-mL samples, three 30-µL samples were pipetted onto glass slides and the rotifers were counted with a stereoscopic microscope at 2×-4× magnification.

Fluorescence

After 12 days, jars were capped with filter paper and inverted to filter water out through the filter paper, leaving only algae. However, after four days, it became evident that a seal had formed, preventing any solution from escaping. Fluorescence measurements were taken on day 18.

After the jars were shaken to minimize residue, a 10-mL sample from each jar was taken and centrifuged at the speed level of 25 for two minutes. 7 mL were then pipetted out, leaving 3 mL of concentrated algal solution. These 3 mL were then homogenized with a Fisher Scientific Touch Mixer for 15 seconds and allowed to sit for approximately 16 hours. The samples were then homogenized a second time, again for 15 seconds, before being analyzed with the Nile red fluorescence method.

Adding 2.5 mg Nile red to 10 mL acetone developed the Nile red-acetone solution. The fluorimeter was zeroed with a blank of distilled water and 100% T was manually determined to be the light level received from the most fluorescent control sample ten minutes after 12 µL of Nile red-acetone solution had been introduced to each control sample. The fluorescence level of each subsequent control sample was then recorded as a percentage of the most luminescent control sample. Once the fluorimeter had been fully calibrated, the other samples were analyzed for Nile red fluorescence. Each non-control sample was first placed in the fluorimeter, without the introduction of Nile red, for the measurement of autofluorescence. Then, ten minutes after the addition of 12 µL of Nile red-acetone solution, the fluorescence of the sample was measured again. Blank solutions of the same compositions utilized for spectrometric blanking were tested with the same fluorescence testing procedure as the non-control samples. Additionally, two 10-mL samples from the control mason jar whose sample achieved the highest luminescence were sent through the previously described centrifugation procedure, homogenized for 15 seconds, and tested with the same fluorescence procedure as used for the non-control samples.

Discussion:

The primary measure of this study was the optical density of algae in the presence or absence of rotifers and/or methoprene as measured in absorbance units at 5, 6, and 12 days. Two secondary measures were also taken. These were the number of live rotifers in a 30-µL sample of algal solution 13 days after initial inoculation as determined by microscopy and the Nile red fluorescence of algae measured as a percentage of the most fluorescent algal sample's reading ten minutes after Nile red exposure.

The optical density of the five test groups was averaged for each group's five jars for each of the three days on which the measurement was taken (FIG. 1; Table 1). Paired two-tailed t-Tests were conducted to investigate the statistical significance of important observed differences between means. At 12 days after inoculation, the average optical densities of the control group (0.96 AU), the group with both methoprene with rotifers (0.69 AU), and the group with double methoprene concentration with rotifers (0.71 AU) were all found to have significantly greater algal densities than the group with only rotifers (0.47 AU). Three t-Tests comparing the day 12 optical density measurements of the control group, A+R+M group, and A+R+2M group to the A+R group yielded P-values of 0.0003, 0.035, and 0.043 respectively. These results suggest that the rotifers in the jars containing only rotifers consumed a substantial portion of the algae over the 12-day period, thereby significantly decreasing the density of the solution. Furthermore, the significant difference between the densities of the A+R and A+R+M groups as well as the significant difference between the A+R group density and the A+R+2M group density suggest that the introduction of methoprene to the rotifer-populated algal system removed the rotifers, enabling greater algal growth and density. The groups with methoprene and rotifers, A+R+M and A+R+2M, were not, however, as dense as the control group (P=0.049; P=0.032 respectively). This difference has two possible causes. The methoprene may have not stifled the rotifers quickly enough to prevent significant algal losses, and/or methoprene at 30 mg/L may be slightly toxic towards *Chlorella* sp.

Figure 2:
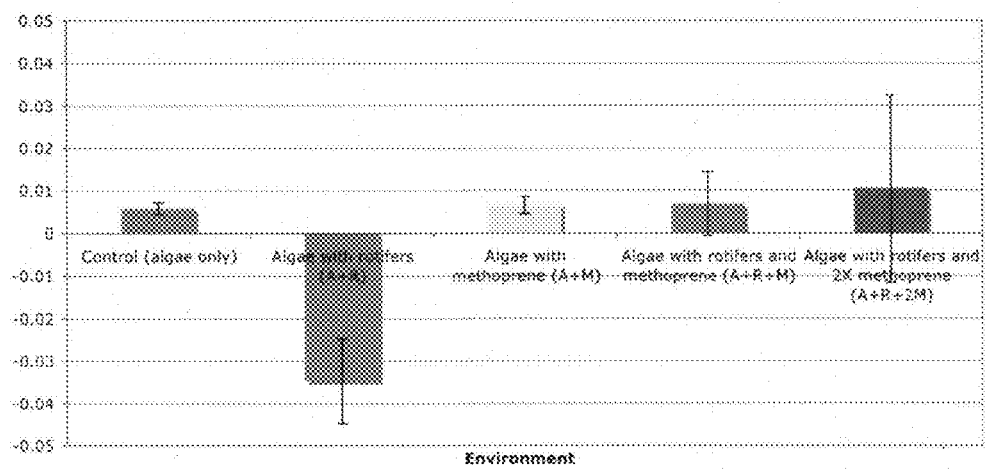
FIG. 2 depicts specific growth rate between 5 and 12 days after inoculation of the five test groups.

The specific growth rate of algae between 5 and 12 days after inoculation was determined in order to further understand the efficacy of methoprene's anti-rotifer ability (FIG. 2). This was calculated using the equation employed by Li and Qin (2005)

$$K = \frac{\log(OD_t) - \log(OD_0)}{T}$$

where K is the specific growth rate, $OD_t$ is the optical density of algae after the interval, $OD_0$ is the algal density before the interval, and T is the duration of the interval in days. The average specific growth rates of the A+R+M and A+M groups were found to be 0.0078 log(AU)/day and 0.0065 log(AU)/day respectively. A t-Test comparing these two means returned a P-value of 0.75. This P-value supports the null hypothesis (that the two specific growth rates are equal). That result, in turn, suggests that during the interval between 5 and 12 days after inoculation, the algae in the A+R+M jars grew undisturbed by rotifers to exhibit a specific growth rate statistically similar to that of the algae in the A+M group. This similarity implies that methoprene did in fact remove nearly all rotifers of the A+R+M group within five days.

The number of live rotifers in a 30-μL sample of algal solution 13 days after initial inoculation was estimated by microscopy. Each of the fifteen jars containing rotifers produced three 30-μL samples. The mean live rotifer population of the A+R group was found to be 8.7 individuals per 30 μL. The 95% confidence interval for this mean was calculated to lie between 7.1 and 10 rotifers per 30 μL. Estimate rotifer counts per 0.5 and 1 liters were further calculated (Table 2). In all 30-μL samples taken from the A+R+M and A+R+2M groups, microscopy yielded zero live rotifers. There was one rotifer in one of the A+R+M samples, but it was dead. These findings also support the hypothesis that the methoprene caused the live rotifer population to become minimal after a few days. The lower methoprene concentration utilized in this project was the 24-hr $LC_{50}$ for *Brachionus plicatilis* found by Marcial et al. (2005). It is therefore little surprise that this concentration, as well as twice the concentration, spares no observable rotifers after 13 days of exposure.

TABLE 1

Mean optical density of algal groups at 5, 6, and 12 days after inoculation ± one standard deviation.

|  | 5 Days | 6 Days | 12 Days |
| --- | --- | --- | --- |
| Control | 0.87 ± 0.03 | 0.94 ± 0.02 | 0.96 ± 0.02 |
| A + R | 0.83 ± 0.08 | 0.84 ± 0.03 | 0.47 ± 0.09 |
| A + M | 0.84 ± 0.02 | 0.89 ± 0.01 | 0.93 ± 0.02 |
| A + R + M | 0.6 ± 0.2 | 0.7 ± 0.2 | 0.7 ± 0.2 |
| A + R + 2M | 0.6 ± 0.2 | 0.7 ± 0.1 | 0.7 ± 0.2 |

TABLE 2

Estimated number of live rotifers in various volumes.

|  | 30 μL | 0.5 liters | 1 liter |
| --- | --- | --- | --- |
| Average | 8.67 | $1.44 \cdot 10^5$ | $2.89 \cdot 10^5$ |
| 95% confidence low limit | 7.09 | $1.18 \cdot 10^5$ | $2.36 \cdot 10^5$ |
| 95% confidence high limit | 10.2 | $1.71 \cdot 10^5$ | $3.41 \cdot 10^5$ |

TABLE 3

Selected results of t-Tests comparing important data groups.
P-Values Yielded from Student's t-Test: Paired, Two-Tailed

| | t-Test input variable groups | | | | |
| --- | --- | --- | --- | --- | --- |
|  | Control and A + R | A + R + M and A + R | A + R + 2M and A + R | Control and A + R + M | Control and A + R + 2M |
| 5 Days | 0.300 | 0.077 | 0.12 | | |
| 6 Days | 0.002 | 0.092 | 0.067 | | |
| 12 Days | 0.0003 | 0.035 | 0.043 | 0.049 | 0.032 |

Example 2

Methoprene at 20 mg/L with acetone at 2% v/v was added to *Chlorella* sp. No growth reduction was observed.

Example 3

Methoprene at a concentration of 30 mg/L or less is added to the algal solution in a rotifer-infested photobioreactor. Acetone at a concentration between 1 and 27 ml/L is also added as an adjuvant. At these concentrations, acetone may (while subjecting the algal crop to minimal harm) act as a surfactant, allowing methoprene to become more dissolved. A cocktail mixture containing optimal concentrations of acetone and methoprene eliminates rotifers. Wait approximately 30 days before renewing the media so that methoprene can biodegrade sufficiently before disposal of water.

Example 4

An approximate 1:1 (w/w) solution of alpha-pinene and propylene glycol is made. Alpha-pinene is the active agent, while propylene glycol is a surfactant. This mixture is added to the algal medium at a concentration equal to or less than 136 mg/L. Daphnia magna and rotofers are controlled in the aquaculture.

Example 5

Materials

Organisms

The *Chlorella* sp. algae used in all tests were purchased from the Carolina Biological Supply Company and were received in a 20-mL solution of algae and Alga-Gro Freshwater Medium. The rotifers used in the biocide toxicity tests were *Brachionus* sp. ordered from Ward's Natural Science and cultured in a dilute hay medium. The rotifers used in the 300-ml microenvironment tests were *Brachionus calyciflorus* ordered from Carolina Biological were cultured in Alga-Gro Freshwater Medium.

Media

For the pesticide toxicity tests, a modified Bristol medium was used to culture and expand the *Chlorella* to test volume and density. This medium was composed of the following components per liter of &stilled water: 0.02 g $(NH_4)_2HPO$ obtained from Mallinckrodt, St Louis, Mo.; 0.25 g $NaNO_3$ from Nurnberg Scientific, Portland Oreg.; 0.025 g 93% $CaCl_2.2H_2O$ from Alpha Aesar, Ward Hill, Mass.; 0.075 g $MgSO_4.7H_2O$ from J. T. Baker Chemical Co., Phillipsburg, N.J.; 0.075 g $K_2HPO_4$ from American Scientific; 0.175 g $KH_2PO_4$ from Mallinckrodt; 0.025 g NaCl from Mallinckrodt; and 6.25 ml artificial seawater salts from Instant Ocean.

For the microenvironment tests, *Chlorella* sp. cultures were expanded and tested in Alga-Gro® Freshwater Medium Biocidal Reagents A 250-mg analytical standard of methoprene was purchased from Sigma Aldrich (St. Louis, Mo.). A 250-mg analytical standard of resmethrin was also purchased from Sigma Aldrich.

Apparatus and Instrumentation

In the biocide toxicity tests, organisms were cultured during the test period in test tubes and were agitated during the testing period on a Polyscience Dual Action Shaker. Optical density measurements in the biocide toxicity tests were taken with a Vernier spectrometer. A calibration of optical algal density and algal cell density was performed with the Vernier spectrometer and a Motic BA300 digital microscope. A VWR Scientific MSE Minor GT-2 centrifuge was used to centrifuge algae for the calibration. Rotifers in the biocide toxicity tests were counted with a Motic stereoscopic dissecting microscope. In the microenvironment tests, organisms were cultured during the test period in 900-ml mason jars (Kerr) without agitation and were illuminated by two 40-W 12-ft General Electric Plant Aquarium EcoBulb fluorescent light bulbs. Optical density measurements in the microenvironment tests were taken with a Fisher Scientific Spectro Master model 410 spectrometer. Dissolved oxygen content was determined with a Vernier dissolved oxygen probe. Rotifers were counted with a Wolfe stereoscopic dissecting microscope.

Methods

Biocide Toxicity Tests 27 ml of *Chlorella* in Alga-Gro Freshwater Medium were added to 300 ml modified Bristol medium and allowed to grow without agitation for 30 hours. The 327 ml of algal solution were then expanded into a total of 700 ml modified Bristol medium and allowed to grow without agitation. After 42 hours, the 700 ml of algal solution were split up into 60 individual test tubes. Each test tube received 10 ml of algal solution, along with 1 ml of rotifer solution (or media) and 4 ml of reagent solution, for a total of 15 ml.

An initial *Brachionus* sp. population of about 30 individuals was cultured without agitation in one 60-ml jar for 3 days. Then, 1 ml of rotifer solution was pipetted into each of the 40 test tubes designated for rotifer toxicity assessment.

The 60 test tubes represented 12 groups, each with five replicates. The test group names and conditions are as follows (Table 4). The group "20M−R" contained algae, 20 mg/l of methoprene, and no rotifers. The group "20M+R" contained algae, 20 mg/l of methoprene, and rotifers. The group "5M+R" contained algae, 5 mg/l of methoprene, and rotifers. The group "5M+A+R" contained 5 mg/l of methoprene, 2% acetone (v/v), and rotifers. The group "2R−R" contained algae, 2.0 mg/l of resmethrin, and no rotifers. The group "2R+R" contained algae, 2.0 mg/l of resmethrin, and rotifers. The group "5R+R" contained algae, 0.5 mg/l of resmethrin, and rotifers. The group "5R+A+R" contained 0.5 mg/l of resmethrin, 2% acetone, rotifers. The group "A−R" contained algae, 2% acetone and no rotifers. The group "A+R" contained algae, 2% acetone and rotifers. The group "R" contained algae and rotifers without any extra reagents. The group "C" contained algae in media only.

TABLE 4

Summary of the naming convention used for groups in the biocide toxicity tests.

| Name | Additives |
| --- | --- |
| 20M − R | 20 mg/L methoprene |
| 20M + R | 20 mg/L methoprene; rotifers |
| 5M + R | 5 mg/L methoprene; rotifers |
| 5M + A + R | 5 mg/L methoprene; 2% acetone; rotifers |
| 2R − R | 2.0 mg/L resmethrin |
| 2R + R | 2.0 mg/L resmethrin; rotifers |
| 5R + R | 0.5 mg/L resmethrin; rotifers |
| 5R + A + R | 0.5 mg/L remsethrin |
| A − R | 0.5 mg/L resmethrin 2% acetone; rotifers |
| A + R | 2% acetone; rotiers |
| Rotifer | rotifers |
| Control | none |

Organisms were cultured and assessed for a test period of 12 days. During the test period, organisms were subjected to agitation at 60 rpm and a photoperiod of 12 hr light, 12 hr dark. The day that organisms were combined into the 60 test tubes was designated as day 0. A 1000-µl sample was removed from each tube for optical density analysis every other day, beginning on day 0. The optical densities of these samples were determined spectrometrically at 680 nm. On days 0, 6, and 12, a 250-µl sample was removed from each of the 1000-µl samples from rotifer-containing groups. Rotifers per 250-µl sample were counted with a dissecting microscope.

In addition, four flasks were filled with 15 ml of four different algal solutions based on the modified Bristol media. These four flasks were monitored during the same test period as the algal solutions in tubes for the purpose of mathematically modeling the interactions between algae and rotifers in the presence and absence of methoprene and resmethrin. The four different solutions were: algae in modified Bristol media (control); algae with rotifers; algae with rotifers and 5 mg/L of methoprene; and algae with rotifers and 0.5 mg/L of resmethrin. Algal density was determined specrometrically at 680 nm every day and rotifer density was determined on days 0, 6 and 12. Both measures were taken with the procedure used for taking those measures in the test tubes.

20 ml of additional algal solution were transferred into two 15-ml sterile plastic tubes for conducting a calibration of algal optical density to cell density. Each tube received 10 ml algal solution and was kept at rest and on a 12-hr light, 12-hr dark photoperiod. On days 1, 2, and 4, a 5-ml sample was taken from each tube. On days 1 and 2, one sample was centrifuged on speed level 3 for 180 seconds, while the other sample was not centrifuged. On day 4 neither sample was centrifuged. The optical density of each sample was then determined spectrometrically at 680 nm and the cell density was determined with a haemocytometer.

Microenvironment Tests 20 ml of *Chlorella* in Alga-Gro Freshwater Medium were expanded to a total of 3.4 liters of Alga-Gro Freshwater medium over 10 days on a 12-hr light, 12-hr dark photoperiod. Algae were then continuously stirred by a sterile magnetic stirring bar and cultured under the same photoperiod. After 7 days, a 100-ml solution of Alga-Gro and 20 grams of glucose was added to the algal solution. 300 ml of the new algal solution were then transferred to each of 11 mason jars. To 6 of the mason jars 10 ml of rotifer solution were added. The other 5 mason jars were used as controls and did not receive any solution (as the rotifer solution contained *Chlorella* and a difference in 3.3% of total volume was not seen as significant in the experimental situation). Prior to transfer to mason jars, the rotifers were cultured for six days from an initial population of about 60 individuals in 100 ml Alga-Gro Freshwater Medium on a photoperiod of 12-hr light, 12-hr dark.

The organisms were cultured on the same photoperiod and were not agitated during the test 8-day period. The day that organisms were combined in the microenvironments was again considered to be day 0. Each day, except for day 6, a 3.0-ml sample was removed from each jar. The dissolved oxygen content of the sample was determined with a dissolved oxygen probe and the optical density of the sample was determined spectrometrically at 680 nm. On days 4 and 8, a 100-μl sample was removed from each 3.0-ml sample for rotifer-containing jar and the sample's rotifer population was determined with a dissecting microscope.

Analysis

Biocide Toxicity

The optical densities of each of the 12 groups in the pesticide toxicity tests were averaged and plotted on a time plot (FIGS. 3 & 4). Standard deviation values and average algal growth rates were calculated for each group and day. T-tests were performed to determine the statistical significance of difference between relevant means. A linear regression model was used to compare the optical density averages of the "20M–R" group and the "C" control group. A linear regression of time against optical density in the control group of tubes was compared with a logarithmic regression model of time against optical density in the control flask. (FIG. 5).

Microenvironment Tests

The optical densities and dissolved oxygen content of both groups were averaged and plotted on a time plot (FIG. 6). Standard deviation values and algal growth rates were calculated for each group and day. A scatter plot and linear regression of dissolved oxygen content against optical density was made for both groups (FIG. 7).

Results

Biocide Toxicity Tests

No living rotifers were observed in any of the samples, including those from the control group, taken during the test period. Neither methoprene, resmethrin, nor acetone, when applied without rotifers, was found to inhibit algal growth. The mean optical densities on day 12 of algal solutions containing 20 mg/L methoprene, 2.0 mg/L resmethrin, and 2% acetone respectively were not significantly different (P>0.05) from the mean optical density of the control group (table 5). Furthermore, a linear regression model of the optical densities of the algal group exposed to methoprene only and the control group gives a line that is approximately 1:1 and an $R^2$ value of 0.982 (FIG. 5). Two groups, 5M+R and 2R–R, were found at day 12 to exhibit a mean optical density significantly lower (P>0.5) than that of the control (table 2).

TABLE 5

P values from t-tests comparing the mean optical densities of the control group and three other non-rotifer groups on days 6 and 12.
Paired t-test: two-tailed P values

| Group | Day 6 | Day 12 |
|---|---|---|
| 20M – RR | 0.224 | 0.715 |
| 2R – R | 0.231 | 0.408 |
| A – R | 0.124 | 0.758 |

TABLE 6

P values from t-tests comparing the mean optical densities of the control group and all other groups on day 12.
Paired t-test: two-tailed P values at day 12

| Group | P value |
|---|---|
| 20M – R | 0.715 |
| 20M + R | 0.129 |
| 5M + R | 0.017 |
| 5M + A + R | 0.323 |
| 2R – R | 0.408 |
| 2R + R | 0.045 |
| 5R + R | 0.740 |
| 5R + A + R | 0.089 |
| A – R | 0.758 |
| A + R | 0.370 |
| Rotifer | 0.610 |

Algal growth in the control group of test tubes (as conceived as change in optical density) was observed to be relatively linear in contrast to the logarithmic growth of algae cultured in the control flask. A line fit to the mean optical densities of the control group over time gave an $R^2$ value of 0.968.

The calibration of optical density at 680 nm to algal cell density gave the equation y=43090x−4759, where y denotes cells per ml and x denotes absorbance units (FIG. 7). This equation can be used to estimate cell density values from absorbance values, although the estimation is rough as the $R^2$ value is only 0.766.

Microenvironment Tests

No live rotifers were observed in any of the samples taken (on days 2, 4, 6, and 8) from the jars. The lack of variation between the control group and the group with rotifers added (in trends in dissolved oxygen content and optical density) is therefore unsurprising (FIG. 8 and FIG. 9). Between days 6 and 12, one tube in the 5R+A+R group and two tubes in the A–R group turned white, displaying signs of bacterial infection. Optical density data taken from infected tubes on days when bacteria were visibly present were discarded from the recorded averages.

The average 24-hour change in dissolved oxygen content correlated moderately ($R^2$=0.663) with the average 24-hour change in optical density in all jars. This suggests, as expected, that the algae produced oxygen as they grew.

Discussion of Results

Biocide Toxicity Tests

No living rotifers were observed in any of the samples, including those from the control group, taken during the test period. The lack of surviving rotifers was likely due to the difference in the concentration of dissolved particles between the rotifers' hay medium and the brackish test medium. If the hay medium contained a considerably greater concentration of dissolved particles than the test medium, the rotifers may have been unable to adjust to the new osmotic pressure and may have died of osmotic shock.

Neither methoprene, resmethrin, nor acetone, when applied without rotifers, was found to inhibit algal growth. Only two groups, 5M+R and 2R-R, were found at day 12 to exhibit a mean optical density significantly lower (P>0.5) than that of the control (table 2). These two lower optical densities could be due to the hay medium's inhibition of algae or effect on the color of the solution, but are more likely due to random chance.

Algal growth in the control group of test tubes was observed to be relatively linear in contrast to the logarithmic growth of algae cultured in the control flask. The relatively linear growth pattern observed in the test tubes was probably due to inhibition of algal growth resulting from the limited surface area and headspace provided by the test tube. The low surface area limits the amount of light harvestable by the algae and the small headspace provides a decreased amount of available carbon dioxide when the tube is capped.

Microenvironment Tests

No live rotifers were observed in any of the samples taken from the jars. This finding was surprising as the media used in the jars was approximately the same as the media that the rotifers were previously cultured in. Additionally, the algae were found to flocculate in all of the jars. Algal flocculation was not observed in the 15-ml biocide toxicity tests. It was hypothesized that the rotifers in the microenvironment tests did not die from osmotic shock, but rather found the algal flocs inedible or unpalatable. This hypothesis was partly based on Lurling and Beekman's (2006) finding that *Chlamydomonas reinhardtii* cells form protective floc-like clumps in the presence of *Brachionus calyciflorus*. To test this hypothesis, 2.18 ml of rotifers at a density of about 3000 rotifers per ml were introduced to a total of 10.18 ml solution containing flocculated algae. Rotifer densities were recorded as the average of three sampled densities at 2, 4, and 5 days after inoculation. The rotifer density in the solution steadily declined from day 2 to day 4 and then reached zero on day 5. While these results are not statistically significant and the rotifers could have died for reasons including intolerable pH, it is unlikely that osmotic shock acted over five days and these results are consistent with the hypothesis that rotifers find flocculating algae unpalatable.

Broad Implications

The findings of the biocide toxicity tests suggest that the transfer from a dense medium to a brackish medium can quickly kill all rotifers transferred. Deliberate temporary changes of solution density and/or salinity therefore provide an effective means of controlling rotifer infestations in algal ponds. Methoprene, resmethrin, and acetone were not found to inhibit algal growth at the experimental concentrations. Biocide formulae containing these agents are viable as selective pesticides against rotifers in algal ponds; the findings of Marical et al. (2005) and Sánchez-Fortúm et al. (2005) suggest that methoprene and resmethrin at concentrations found in this study to be nontoxic to algae are significantly harmful to rotifers An ideal formula cheaply eliminates all rotifers while exhibiting minimal toxicity to algae, humans, or the surrounding ecology.

Algae grown in test tubes were found to exhibit a relatively linear growth pattern, in contrast to the growth patterns of algae grown in the flasks or jars. If algae growing at a relatively linear rate are desired for any purpose in future research, it is suggested that the algae be grown in a small (about 20-ml) test tube with about 5 ml of headspace.

What is claimed is:

1. A method comprising:
   a. growing algae in a media containing a biocide, wherein the biocide controls a grazer population; and
   b. harvesting the algae;
   wherein the biocide is methoprene and the methoprene is added to the media to form a concentration of between 1 and 100 mg/L.

2. The method of claim 1 wherein the media further comprises an adjuvant, wherein the adjuvant comprises acetone, propylene glycol, or nonylphenylethoxylate.

3. The method of claim 1 wherein the media further comprises an adjuvant, wherein the adjuvant comprises an anionic surfactant, a cationic surfactant, a non-ionic surfactant, an amphoteric surfactant or a combination thereof.

4. The method of claim 3 wherein the anionic surfactant is selected from the group consisting of fatty acid sulphates, fatty acid ether sulphonates and their salts; alkyl aryl sulphonates, a sulphonate of dodecyl benzene and their salts, fatty acid salts, mono-,di-,tri-aryl poly-glycolether phosphoric acid esters and their salts.

5. The method of claim 3 wherein the cationic surfactant is selected from the group consisting of quatenary ammonium salt and a phenyl derivative thereof.

6. The method of claim 3 wherein the non-ionic surfactant is selected from the group consisting of polyethoxylated castor oil, sorbitan, sorbitan esters, fatty alcohols, acids and esters, alkylphenols, ethoxylated nonyl phenol, and block polymers of ethylene and propylene oxide and their alkyl, aryl and alkylaryl condensates.

7. The method of claim 3 wherein the amphoteric surfactant is alkyl betaine.

8. The method of claim 1 wherein the algae is green algae, red algae, brown algae, golden-brown algae, blue-green algae (cyanobacteria), diatoms, or a combination thereof.

9. The method of claim 1 wherein the algae is *Amphipleura, Chlorella, Botryococcus, Dunaliella, Gracilaria, Nannochloris, Nannochlorpsis, Pleurochrysis carterae, Sargassum, Scendesmus, Spirulina, Ulva* or a combination thereof.

10. The method of claim 1 wherein the grazers comprise rotifers, moina, daphnids or a combination thereof.

11. The method of claim 1 wherein the algae grown in the presence of a grazers grows to within 80-100% of a control algae absent grazers.

* * * * *